(12) United States Patent
Mehta et al.

(10) Patent No.: US 10,888,878 B2
(45) Date of Patent: *Jan. 12, 2021

(54) METHODS, SYSTEMS AND APPARATUS FOR MANIPULATING PARTICLES

(71) Applicant: Sartorius Stedim North America Inc., Bohemia, NY (US)

(72) Inventors: Sunil Mehta, Morrisville, NC (US); Tod Herman, Hillsborough, NC (US); Joe McMahon, Chapel Hill, NC (US); Stephen Wilson, Kew (AU); Ian Fitzpatrick, Elwood (AU); Timothy Craig, Tooradin (AU)

(73) Assignee: Sartorius Stedim North America Inc., Bohemia, NY (US)

( * ) Notice: Subject to any disclaimer, the term of this patent is extended or adjusted under 35 U.S.C. 154(b) by 540 days.

This patent is subject to a terminal disclaimer.

(21) Appl. No.: 15/806,670

(22) Filed: Nov. 8, 2017

(65) Prior Publication Data

US 2018/0065127 A1 Mar. 8, 2018

Related U.S. Application Data

(63) Continuation of application No. 13/499,807, filed as application No. PCT/US2010/051631 on Oct. 6, 2010, now Pat. No. 9,839,920.

(Continued)

(51) Int. Cl.
*B04B 5/04* (2006.01)

(52) U.S. Cl.
CPC .... *B04B 5/0442* (2013.01); *B04B 2005/0471* (2013.01); *B04B 2005/0492* (2013.01)

(58) Field of Classification Search
CPC .......... B04B 5/0442; B04B 2005/0471; B04B 2005/0492; B04B 15/00

(Continued)

(56) References Cited

U.S. PATENT DOCUMENTS 3,672,564 A 6/1972 Schlutz et al.
4,056,224 A * 11/1977 Lolachi ............... A61M 1/3693
                                                494/18

(Continued)

FOREIGN PATENT DOCUMENTS

EP 0 260 034 3/1988
EP 0260034 A1 * 3/1988 ........... B04B 5/0442

(Continued)

OTHER PUBLICATIONS

JPH0515813 Description Espacenet Machine Translation.*

(Continued)

*Primary Examiner* — Walter D. Griffin
*Assistant Examiner* — Shuyi S. Liu
(74) *Attorney, Agent, or Firm* — Myers Bigel, P.A.

(57) ABSTRACT

An apparatus for manipulating particles includes: a rotor rotatable at a speed about an axis, the rotor having an outer periphery and front and rear opposite sides; at least one chamber mounted on the rotor, each chamber having an inlet and an outlet; an umbilical assembly rotatable about the axis; and a drive mechanism configured to rotate the umbilical assembly at about one-half the speed of the rotor. The umbilical assembly includes: a curvilinear guide tube connecting to a drum at the rear side of the rotor; a flexible conduit residing in the guide tube; and first and second elongate passageways for each chamber extending through the conduit, wherein the first passageway is in fluid communication with the inlet of a respective chamber and the second passageway is in fluid communication with the outlet of the respective chamber. The passageways are held in a spaced-apart relationship relative to one another.

23 Claims, 26 Drawing Sheets

Related U.S. Application Data

(60) Provisional application No. 61/249,058, filed on Oct. 6, 2009.

(58) Field of Classification Search
USPC ............................................ 494/10, 12, 18
See application file for complete search history.

(56) References Cited

U.S. PATENT DOCUMENTS

| | | | |
|---|---|---|---|
| 4,114,802 | A | 9/1978 | Brown |
| 4,146,172 | A | 3/1979 | Cullis et al. |
| 4,350,283 | A | 9/1982 | Leonian |
| 4,372,484 | A | 2/1983 | Larsson et al. |
| 4,778,444 | A | 10/1988 | Westberg et al. |
| 4,939,087 | A | 7/1990 | Van Wie et al. |
| 5,656,163 | A * | 8/1997 | Brown ............... B01D 21/26 210/360.1 |
| 5,665,048 | A | 9/1997 | Jorgensen |
| 6,051,146 | A | 4/2000 | Green et al. |
| 6,916,652 | B2 | 7/2005 | Petrecca et al. |
| 2004/0127841 | A1* | 7/2004 | Briggs ............... A61K 41/0066 604/6.01 |
| 2005/0059540 | A1* | 3/2005 | Skinkle ............... B04B 5/0442 494/48 |

FOREIGN PATENT DOCUMENTS

| | | | |
|---|---|---|---|
| EP | 0693969 | 9/2000 | |
| JP | S4720306 | 6/1972 | |
| JP | S54-082716 | 7/1979 | |
| JP | S56-065647 | 6/1981 | |
| JP | S 61284254 | 12/1986 | |
| JP | S63-014628 | 3/1988 | |
| JP | H02049788 | 10/1990 | |
| JP | H0515813 | * 1/1993 | ..... B04B 2005/0471 |
| JP | S58 3747 | 1/1993 | |
| JP | H06-505675 | 6/1994 | |
| JP | H11-504857 | 5/1999 | |
| JP | 2006175232 | 7/2006 | |
| JP | H07-502676 | 1/2010 | |
| WO | WO 93/12887 | 7/1993 | |
| WO | WO 94/08689 | 4/1994 | |
| WO | WO 97/23297 | 7/1997 | |
| WO | WO 01/18396 | 3/2001 | |
| WO | WO 2009/062714 | 5/2009 | |

OTHER PUBLICATIONS

Translation of Notice of Preliminary Rejection for Korean Patent Application No. 10-2017-7036986 dated Mar. 16, 2018, 9 pages.
Communication pursuant to Article 94(3) EPC for EP application No. 10771586.4 mailed May 22, 2018, 4 pages.
Extended European Search Report for EP Application No. 18153768.9 dated Sep. 17, 2018, 7 pages.
EP Communication for corresponding EP Application No. 10 771 586.4 dated Jul. 20, 2017, 6 pages.
Translation of Notice of Preliminary Rejection for Korean Application No. 10-2012-7011664 dated Jan. 10, 2017, 16 pages.
The International Search Report and the Written Opinion for PCT/US2010/051631 dated Feb. 18, 2011.
The International Preliminary Report for PCT/US2010/051631 dated Apr. 19, 2012.

* cited by examiner

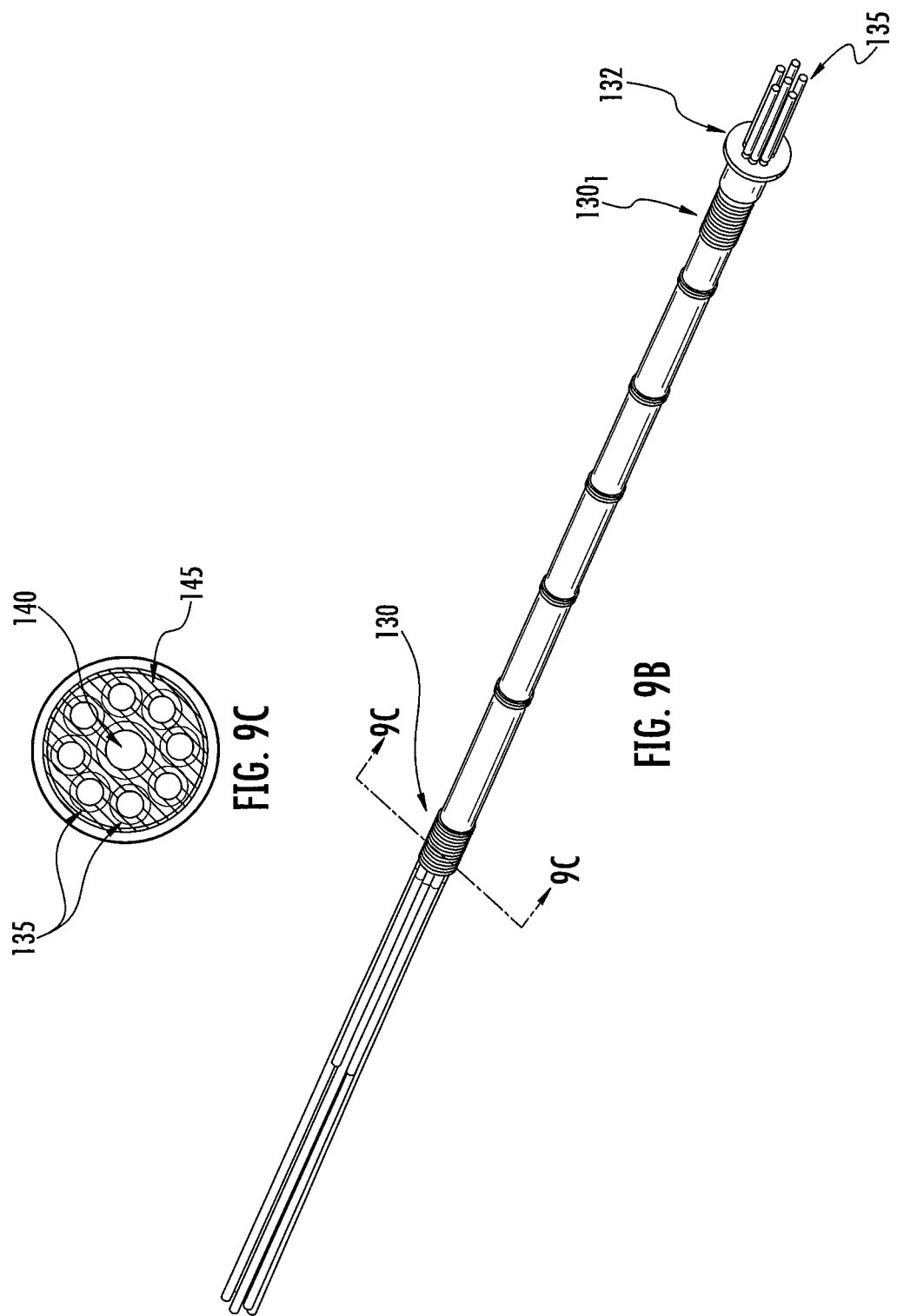

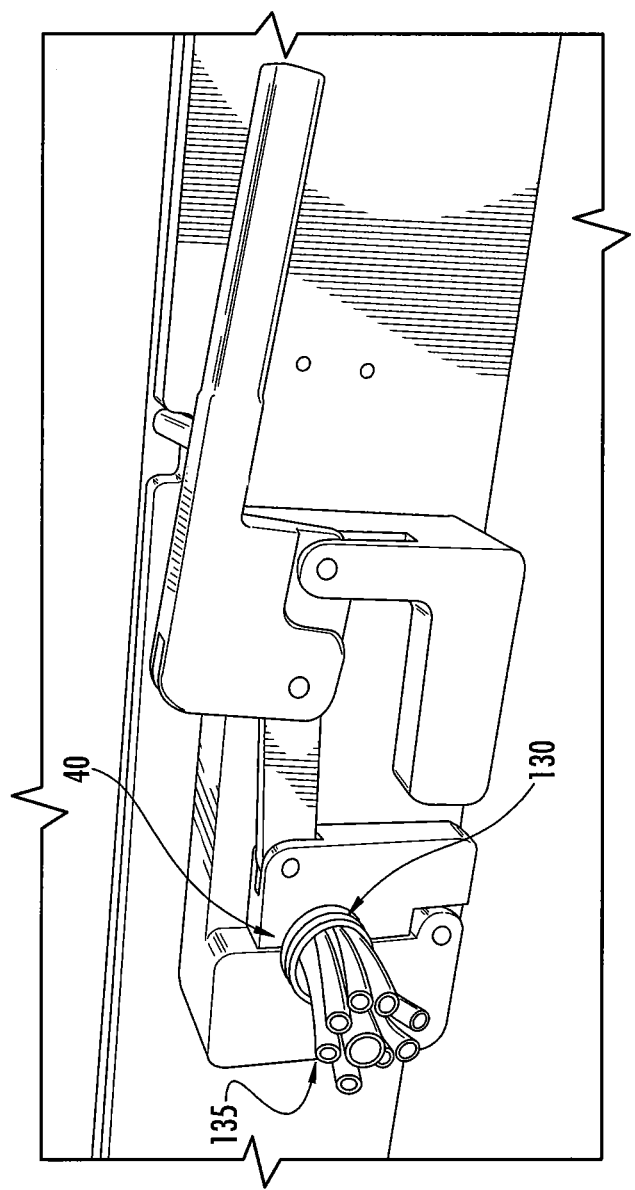

Manual Control

CENTRIFUGE/PERISTALTIC PUMPS

| | Speed | | REV | Stop | FWD |
|---|---|---|---|---|---|
| Pump A | | (ml/min) | ▼ | ■ | ▲ |
| Pump B | | (ml/min) | ▼ | ■ | ▲ |
| Pump C | | (ml/min) | ▼ | ■ | ▲ |
| Pump D | | (ml/min) | ▼ | ■ | ▲ |
| Media Pump | | (ml/min) | ▼ | ■ | ▲ |
| Centrifuge | | (g) | | ■ | ▲ |

PINCH VALVES

| Open | PV1 (Open) | Close |
|---|---|---|
| Open | PV2 (Open) | Close |
| Open | PV3 (Open) | Close |
| Open | PV4 (Open) | Close |
| Open | PV5 (Open) | Close |
| Open | PV6 (Open) | Close |
| Open | PV7 (Open) | Close |
| Open | PV8 (Open) | Close |
| Open All | | Close All |

BUBBLE SENSORS

Bubble Sensor 1: Air,uid    Bubble Sensor 3: Air,uid
Bubble Sensor 2: Air,uid    Bubble Sensor 4: Air,uid Main Screen

FIG. 18

Recipes - Concentrate, Wash & Harvest

Recipe Name

Current Selection: s.s (s...s)
Estimated Processing Time (# vessels): #####h ##m Main Screen Parameters Current Recipe

- Application Type:
- Recipe Name:
- Bioreactor Volume: (l)
- Vessel Size: (ml)
- Wash Volume: (No. of Changes)
- Harvest Flow Rate: (ml/min)
- Harvest Initial Dump Volume: (ml/vessel)
- Harvest Collection Volume: (ml/vessel)
- Outlet Waste Tube ID: (in)
- Outlet Waste Tube Length: (ft)
- Outlet Media Tube ID: (in)
- Outlet Media Tube Length: (ft)
- Cell Harvest Tube ID: (in)
- Cell Harvest Tube Length: (ft)

Active Vessels: A B C D

- Centrifuge Speed: (g)
- Normal Flow Rate: (ml/min)
- Starting Flow Rate: (ml/min)
- Time to Establish Bed: (min)
- Flow Rate Ramp-Up Time: (min)

Download to controller

FIG. 19

METHODS, SYSTEMS AND APPARATUS FOR MANIPULATING PARTICLES

CROSS-REFERENCE TO RELATED APPLICATIONS

This application is a continuation of U.S. application Ser. No. 13/499,807, filed Jul. 16, 2012, which is a 35 U.S.C. § 371 national phase application of PCT International Application No. PCT/US2010/051631, filed Oct. 6, 2010, which claims priority from U.S. Provisional Patent Application No. 61/249,058, filed Oct. 6, 2009, the disclosures of which are hereby incorporated herein by reference in their entireties.

FIELD OF THE INVENTION

The present invention is related to methods, systems, and apparatus that are used for transferring and manipulating particles, as well as components that are useful in systems and apparatus for transferring and manipulating particles, such as continuous flow centrifuges.

BACKGROUND

Conventional continuous flow centrifuges raise several concerns with regard to leaking and/or contamination. For example, in conventional continuous flow centrifuges, when a length of tubing is fixedly attached to the rotation axis of a device which contains the fluid material to be centrifuged, the entire length of tubing must be rotated by use of rotating seals or other means to avoid twisting the tubing. However, these seals too frequently become the source of leaks and/or contamination.

Umbilical-like arrangements for use with continuous flow centrifuges have been disclosed in, for example, U.S. Pat. Nos. 4,216,770, 4,419,089, 4,389,206, and 5,665,048. However, these solutions do not adequately address the high stresses and strains imparted on the tubes due to the g-forces created by rotating the centrifuge at high speeds and/or due to the continuous fluid flow necessary to substantially immobilize particles. Moreover, rotating the centrifuge at high speeds creates increased "partial" twisting action of the umbilical system and the tubes contained therein, and the arrangements disclosed to date do not allow the umbilical system and the tubes contained therein to be rotated at a high rate of speed for an acceptable amount of time before failing. In other words, it is believed that the aforementioned solutions simply do not allow the systems to be "scaled up" to an appreciable degree and do not allow the system to be rotated at high rates of speed without rapid and catastrophic failure of the tubing system.

For small-scale operations, the elimination of rotary seals or the like may address some contamination concerns with regard to conventional continuous flow centrifuges. However, other contamination concerns remain. For example, the fluid flow paths may become contaminated over time (e.g., after more than one use), unless the utmost care is taken in cleaning and/or sterilization. A disposable fluid flow path (or multiple disposable fluid flow paths) could eliminate the need for expensive and time-consuming cleaning, and could help ensure contamination-free operations. The disposable fluid flow paths would preferably be easily replaceable, and would be adaptable to a system that would allow the system as a whole to be "scaled-up," as discussed above.

SUMMARY

According to some embodiments of the present invention, an apparatus for manipulating particles includes: a rotor rotatable at a speed about an axis, the rotor having an outer periphery and front and rear opposite sides; at least one chamber mounted on the rotor, each chamber having an inlet and an outlet; an umbilical assembly rotatable about the axis; and a drive mechanism configured to rotate the umbilical assembly at about one-half the speed of the rotor. The umbilical assembly includes: a curvilinear guide tube connecting to a drum at the rear side of the rotor; a flexible conduit residing in the guide tube; first and second elongate passageways for each chamber extending through the conduit, wherein the first passageway is in fluid communication with the inlet of a respective chamber and the second passageway is in fluid communication with the outlet of the respective chamber. The passageways are held in a spaced-apart relationship relative to one another.

In some embodiments, the first and second passageways for each chamber comprise corresponding first and second flexible tubes that extend through at least a major portion of a length of the conduit. Potting material within the conduit is configured to hold the tubes in the spaced-apart relationship relative to the one another and hold the tubes in a spaced-apart relationship relative to the conduit. The potting material may be further configured to restrict movement of the tubes relative to the conduit and/or restrict movement of the tubes relative to one another.

In some embodiments, the umbilical assembly further includes a flexible member extending through at least a major portion of a length of the conduit, wherein the flexible member extends substantially along a centerline of the conduit, and wherein the flexible tubes surround the flexible member. The potting material may be further configured to restrict movement of the tubes relative to the flexible member.

Each chamber may be a flexible translucent or transparent fluid chamber, and the apparatus may further include at least one chamber holder pivotably mounted to the front side of the rotor, wherein each chamber holder is configured to releasably enclose a respective chamber. Each chamber holder may include a window to allow visual access to the enclosed chamber.

Each chamber may include a substantially conical body portion and a flange extending about at least a portion of a perimeter of the conical body portion. The flange includes an inlet fluid path and an outlet fluid path, wherein the first flexible tube connects with the flange inlet fluid path of a respective chamber and the second flexible tube connects with the flange outlet fluid path of the respective chamber. The flange inlet and outlet paths may be substantially parallel along a segment extending from a point at which the first and second tubes connect with the flange inlet and outlet paths.

In some embodiments, the conduit and passageways are integrated as a flexible extrusion with an outer wall and internal elongate channels that define the spaced-apart passageways.

Each chamber may include a substantially conical body portion and a flange extending about at least a portion of a perimeter of the conical body portion. The flange includes an inlet fluid path and an outlet fluid path, wherein the first passageway is in fluid communication with the flange inlet fluid path of a respective chamber and the second passageway is in fluid communication with the flange outlet fluid path of the respective chamber. A first tube may connect the first passageway and the flange inlet fluid path and a second tube may connect the second passageway and the flange outlet fluid path, and the flange inlet and outlet paths may be substantially parallel along a segment extending from a point at which the first and second tubes connect with the flange inlet and outlet paths. A connector may be included at each of the first and second passageways, with one connector configured to connect the first tube with the first passageway and the other connector configured to connect the second tube with the second passageway.

The drive mechanism may include gears. The gears may be at least partially enclosed by the drum. The conduit may include proximal and distal opposite ends, wherein the conduit distal end connects to the rotor. In some embodiments, the conduit distal end has a substantially hexagonally shaped coupling.

In some embodiments, the umbilical assembly includes a plurality of spaced-apart flexible holders in the conduit to hold the passageways in the spaced-apart relationship.

In some embodiments, the at least one chamber comprises a plurality of chambers mounted on the rotor in a spaced-apart relationship.

According to other embodiments of the present invention, a disposable fluid path for use with a continuous flow centrifuge including a rotor having an outer periphery and front and rear opposite sides includes: at least one chamber mounted on the rotor, each chamber having an inlet and an outlet; a flexible conduit curving around the outer periphery of the rotor and connecting to the rotor; first and second flexible tubes for each chamber extending through the conduit, wherein the first tube is in fluid communication with the inlet of a respective chamber and the second tube is in fluid communication with the outlet of the respective chamber; and potting material within the conduit, wherein the potting material is configured to hold the tubes in a spaced-apart relationship. The potting material may be further configured to restrict movement of the tubes relative to the conduit and/or relative to one another.

In some embodiments, the disposable fluid path further includes a flexible member extending through the conduit, wherein the flexible member extends substantially along a centerline of the conduit, and wherein the flexible tubes surround the flexible member. The potting material may be further configured to restrict movement of the tubes relative to the flexible member.

According to other embodiments of the present invention, an umbilical assembly for use with a continuous flow centrifuge having a rotor and at least one chamber having an inlet and an outlet attached to the rotor includes: a curvilinear guide tube connecting to a drum at the rear side of the rotor; a flexible conduit residing in the tube; first and second flexible tubes for each chamber extending through at least a major portion of a length of the conduit, wherein the first tube is in fluid communication with the inlet of a respective chamber and the second tube is in fluid communication with the outlet of the respective chamber; and potting material within the conduit, wherein the potting material is configured to hold the tubes in a spaced-apart relationship. The potting material may be further configured to restrict movement of the tubes relative to the conduit and/or relative to one another.

In some embodiments, the umbilical assembly further includes a flexible member extending through the conduit, wherein the flexible member extends substantially along a centerline of the conduit, and wherein the flexible tubes surround the flexible member. The potting material may be further configured to restrict movement of the tubes relative to the flexible member.

According to other embodiments of the present invention, an umbilical assembly for use with a continuous flow centrifuge having a rotor and at least one chamber attached to the rotor includes a flexible extrusion comprising first and second spaced-apart passageways therein for each chamber, wherein the first passageway is in fluid communication with an inlet of a respective chamber and the second passageway is in fluid communication with an outlet of the respective chamber.

According to other embodiments of the present invention, a disposable fluid path for use with a continuous flow centrifuge having a rotor includes a first disposable section and a second disposable section. The first disposable section includes: at least one chamber configured to be held on the rotor, wherein each chamber has an inlet and an outlet; and first and second tubes for each chamber, wherein the first tube is configured to be in fluid communication with the inlet of a respective chamber and the second tube is configured to be in fluid communication with the outlet of the respective chamber. The second disposable section includes: tubing in fluid communication with at least one container; the tubing configured to fit within one or more valves.

In some embodiments, the first disposable section includes return tubing in fluid communication with the at least one container. In some embodiments, the second disposable section includes return tubing in fluid communication with the at least one container. The first and second disposable sections may be configured to be connected using a sterile tube welding process.

In some embodiments, each chamber is a flexible translucent or transparent fluid chamber, wherein the chamber includes a substantially conical body portion. The chamber also includes a flange extending about at least a portion of a perimeter of the substantially conical body portion, and the flange includes an integral inlet fluid path and an integral outlet fluid path. The first tube connects with the flange inlet fluid path of a respective chamber and the second tube connects with the flange outlet fluid path of the respective chamber. The flange inlet and outlet fluid paths may be substantially parallel along a segment extending from the point at which the first and second tubes connect with the flange inlet and outlet fluid paths.

According to other embodiments of the present invention, a centrifugal fluid processing system includes: a housing having an interior cavity with an access aperture extending from an external surface of the housing to the interior cavity; a plurality of fluid chambers held in spaced apart relationship on a rotor in the interior cavity; a flexible conduit holding a plurality of flexible tubes in a spaced-apart relationship therein, the flexible conduit extending from a location that is external to the housing through the access aperture and into the interior cavity, wherein the plurality of tubes includes first and second tubes for each chamber, wherein the first tube is in fluid communication with an inlet of a respective chamber and the second tube is in fluid communication with an outlet of the respective chamber, wherein the flexible conduit comprises a solid flexible material that substantially fills an internal volume of the conduit and surrounds the flexible tubes, with the solid flexible material configured to hold the flexible tubes in the spaced-apart relationship; a substantially rigid curvilinear guide tube holding a portion of the flexible conduit in the interior cavity; and a drive mechanism configured to rotate the guide tube at a first speed and the rotor and the fluid chambers at a second speed, wherein the second speed is about twice the first speed.

According to other embodiments of the present invention, a centrifugal fluid processing system includes: a housing having an interior cavity with an access aperture extending from an external surface of the housing to the interior cavity;

a plurality of fluid chambers held in spaced apart relationship on a rotor in the interior cavity; a flexible conduit including a plurality of spaced-apart passageways therein, the flexible conduit extending from a location that is external to the housing through the access aperture and into the interior cavity, wherein the plurality of tubes includes first and second passageways for each chamber, wherein the first passageway is in fluid communication with an inlet of a respective chamber and the second passageway is in fluid communication with an outlet of the respective chamber; a substantially funnel-shaped support with an open center passage, the support having a shape that tapers outward as it extends further into the interior cavity, wherein the support surrounds the flexible conduit with a centerline of the funnel shaped support being in line with a centerline of the access aperture; a substantially rigid curvilinear guide tube holding a portion of the flexible conduit in the interior cavity; and a drive mechanism configured to rotate the guide tube at a first speed and the rotor and the fluid chambers at a second speed, wherein the second speed is about twice the first speed.

According to other embodiments of the present invention, a centrifugal fluid processing system includes: a housing having an interior cavity with an access aperture extending from an external surface of the housing to the interior cavity; a plurality of flexible translucent or transparent fluid chambers having an inlet and an outlet held in spaced-apart relationship on a rotor in the interior cavity, wherein each chamber includes a substantially conical body portion, each chamber including a flange extending about at least a portion of a perimeter of the conical body portion, the flange including an inlet fluid path and an outlet fluid path, wherein the flange inlet fluid path is in fluid communication with the inlet of the chamber and the flange outlet fluid path is in fluid communication with the outlet of the chamber; a flexible conduit including a plurality of elongate spaced-apart passageways therein, the flexible conduit extending from a location that is external to the housing through the access aperture and into the interior cavity, wherein the plurality of passageways includes first and second passageways for each chamber, and wherein the first passageway is in fluid communication with the flange inlet fluid path of a respective chamber and the second passageway is in fluid communication with the flange outlet fluid path of the respective chamber; a substantially rigid curvilinear guide tube holding a portion of the flexible conduit in the interior cavity; a drive mechanism configured to rotate the guide tube at a first speed and the rotor and the fluid chambers at a second speed, wherein the second speed is about twice the first speed; and a plurality of substantially rigid chamber holders in the interior cavity, each sized and configured to releasably hold a respective flexible chamber attached to the rotor.

According to other embodiments of the present invention, a method of manipulating particles includes providing: at least one chamber on a rotor having an outer periphery, each chamber having an inlet and an outlet; a flexible conduit with first and second spaced-apart passageways therein for each chamber, wherein the first passageway is in fluid communication with the inlet of a respective chamber and the second passageway is in fluid communication with the outlet of the respective chamber; and a substantially rigid curvilinear guide tube holding a portion of the conduit therein and curving around the outer periphery of the rotor. The method further includes: rotating the rotor and the at least one chamber at a first speed, thereby creating a centrifugal force field; rotating the guide tube and conduit therein at a second speed, wherein the second speed is about one-half the first speed, thereby inhibiting the first and second passageways for each chamber from fully twisting; flowing media and particles into a respective chamber using the first passageway, wherein a continuous flow of media and particles creates a fluid force that substantially opposes the centrifugal force field, thereby immobilizing at least some of the particles in a fluidized bed in the respective chamber; and flowing media out of the respective chamber and through the second passageway.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE FIGURES

FIG. 9B illustrates a portion of an umbilical assembly according to some embodiments of the present invention and FIG. 9C is a cross-sectional view of the umbilical assembly of FIG. 9B.

FIG. 14B illustrates a clamp for use with an umbilical assembly according to some embodiments of the present invention.

FIGS. 18-20 are simulated screenshots of a display associated with systems according to some embodiments of the present invention.

DETAILED DESCRIPTION AND EMBODIMENTS OF THE INVENTION

Figure 1:
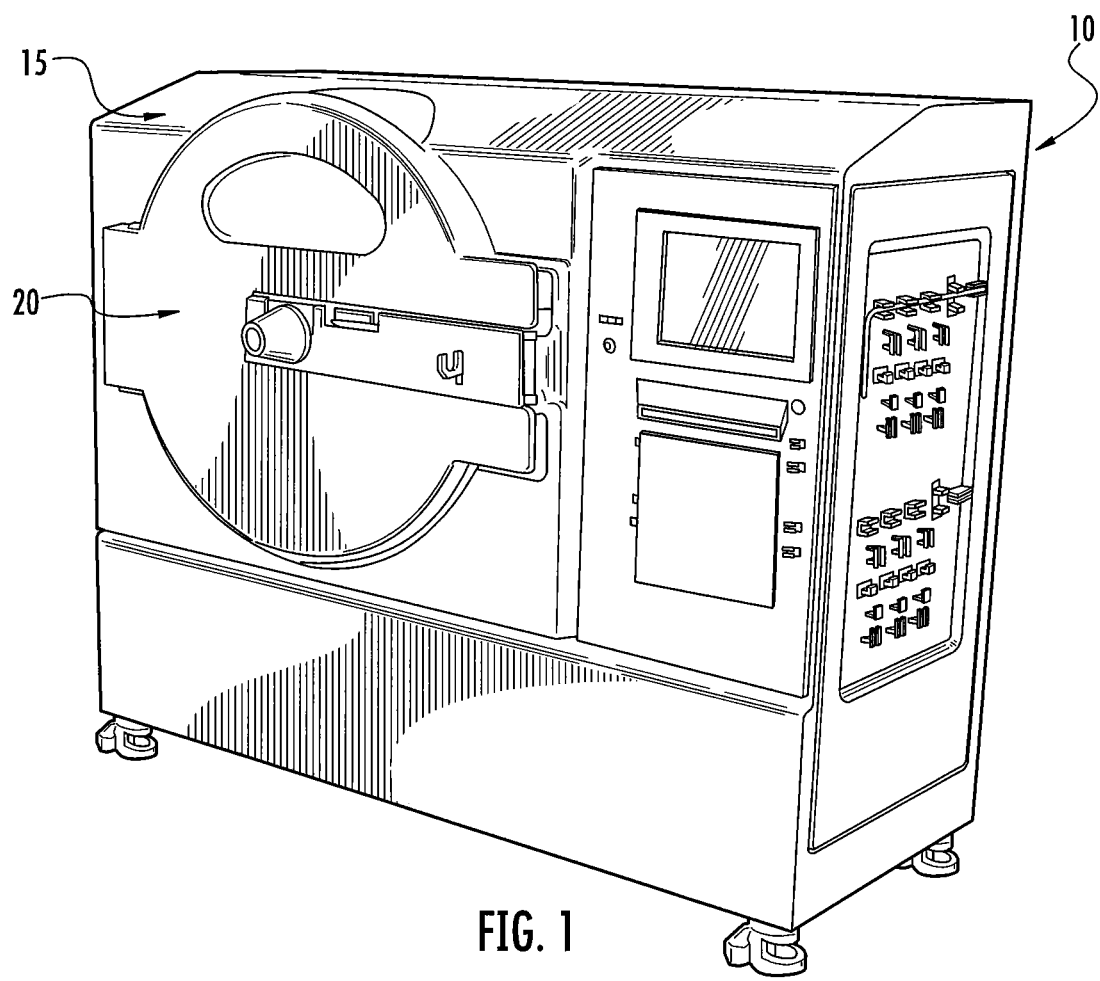
FIG. 1 is a side perspective view of a system according to some embodiments of the present invention.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Apparatus, systems, and methods for the manipulation of particles are disclosed herein. Also, components useful in apparatus and systems for the manipulation of particles are disclosed herein.

Figure 2:
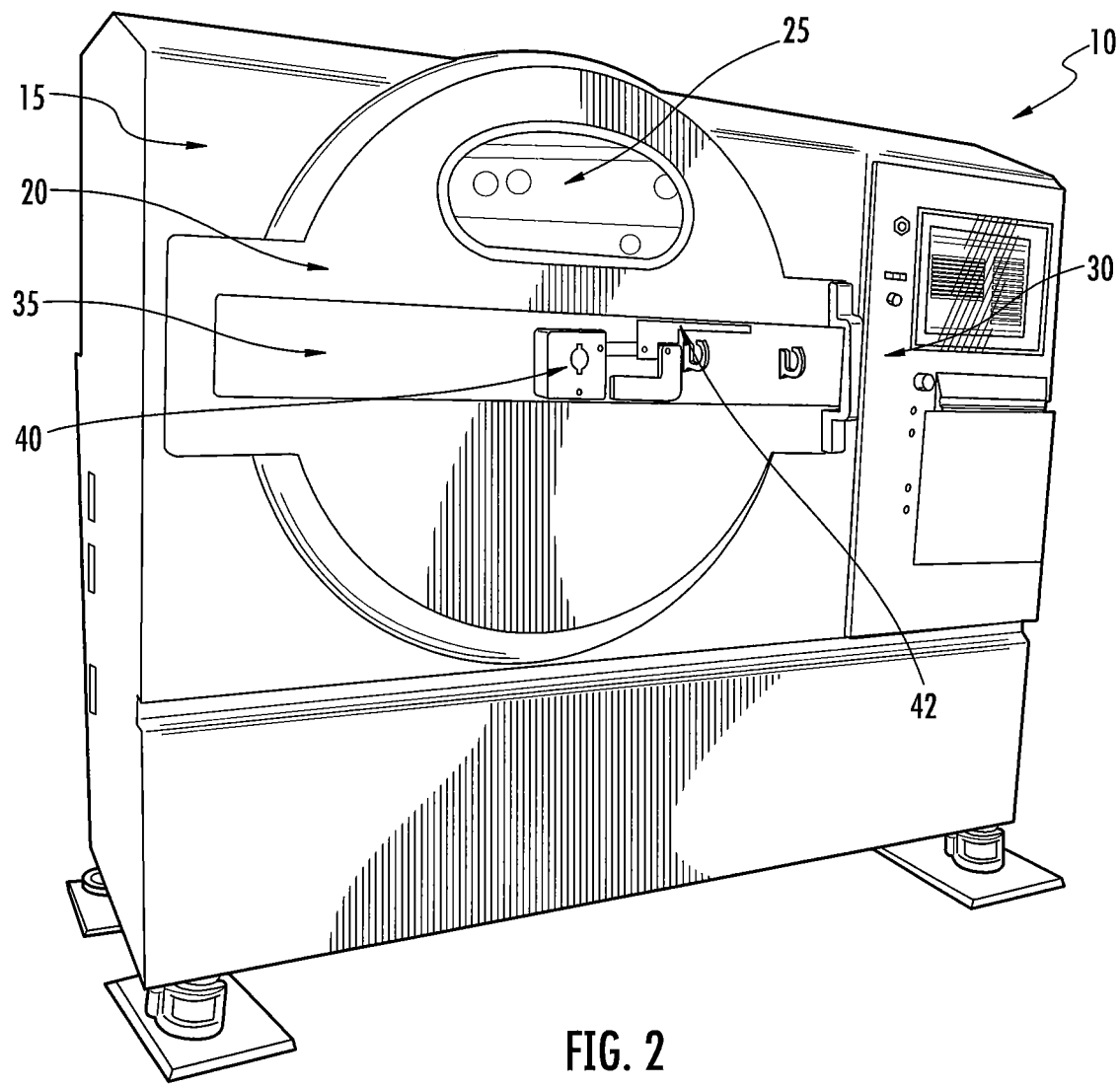
FIG. 2 is an opposing side perspective view of the system of FIG. 1.

FIGS. 1 and 2 illustrate a system 10 according to some embodiments of the present invention. The system 10 includes an enclosure or housing 15 and a door 20. The door 20 provides access to the internal components of the system 10, which are described in more detail below. The door 20 may include a window 25 to provide visual access to the internal components. The door 20 can be hingedly attached to the enclosure 15, and can be opened by a handle 30, for example.

The system 10 includes a flange 35. The flange 35 may be included with the door 20, or may be a separate component (i.e., when the door 20 is opened, the flange 35 remains in place). The flange 35 includes an access aperture 40, through which conduit with channels, passageways, or tubing therein, for example, can extend, as described in more detail below. The door 20 and/or the flange 35 can include a clamp 42, which is configured to hold the conduit in place and/or release the conduit.

Figure 3:
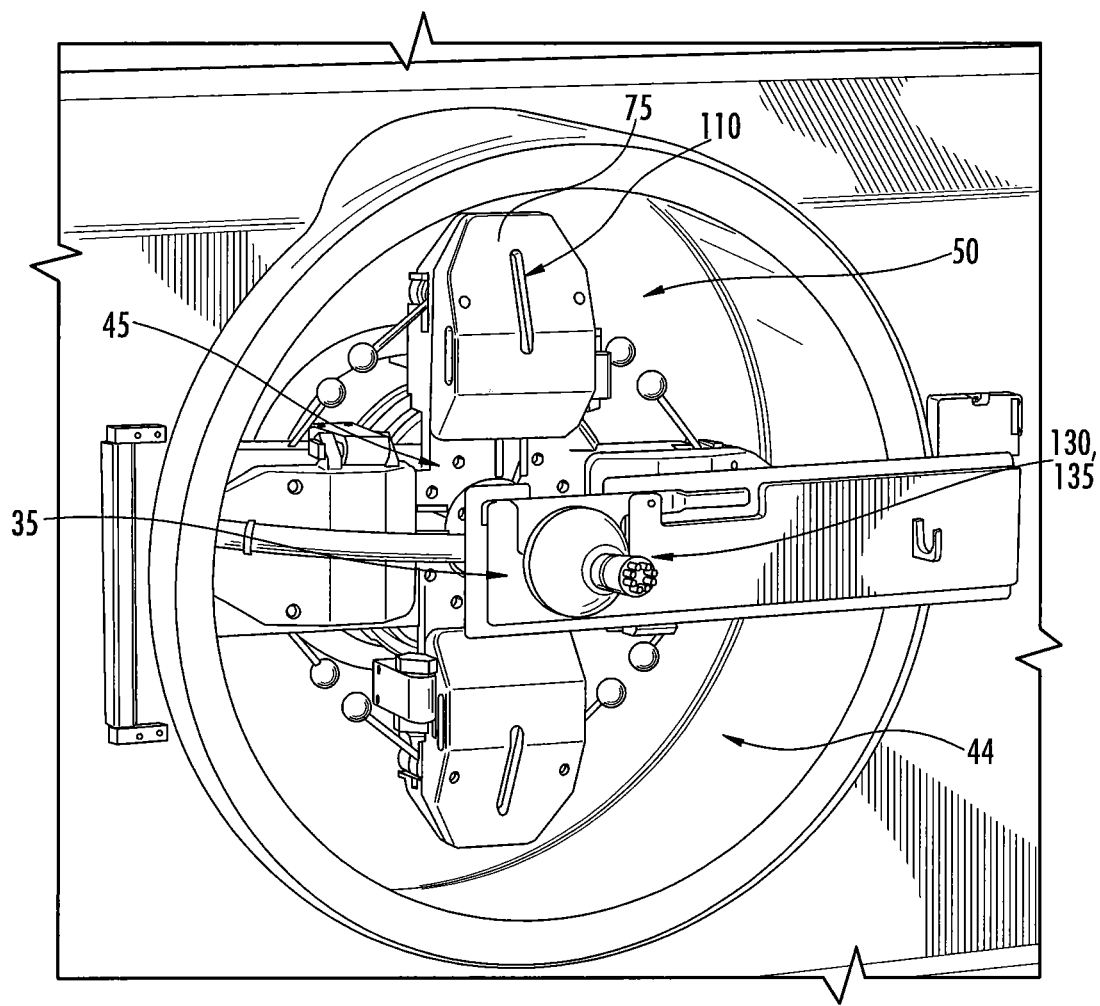
FIG. 3 is a side perspective view of an interior portion of the system of FIG. 1, illustrating internal components.
Figure 4:
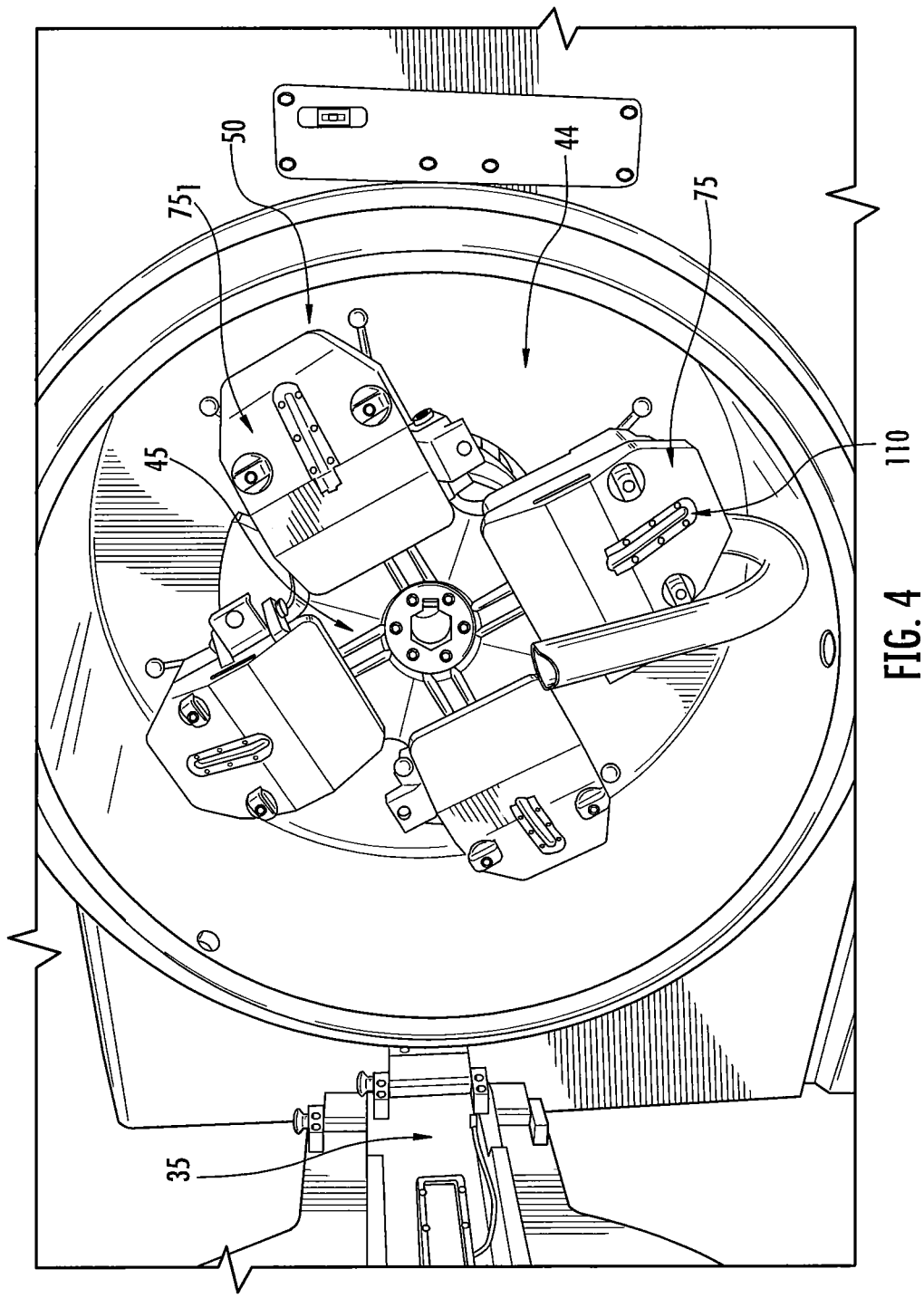
FIG. 4 is a side perspective view of an interior portion of the system of FIG. 1, illustrating internal components.

FIG. 3 illustrates the system 10 with the door 20 opened. As shown, the flange 35 remains in place. FIG. 4 illustrates the system 10 with the door 20 and the flange 35 pivotably opened. The enclosure or housing has an interior cavity 44, which can be seen in FIGS. 3 and 4 when the door 20 and/or the flange 35 have been opened. Some of the internal components of the system 10 are contained in the interior cavity 44, as seen in FIGS. 3 and 4. Notably, a rotor 45 is configured to be rotatable about an axis. At least one fluid chamber 50 is attached to or mounted on the rotor 45, so as to be held in a fixed spaced-apart relationship and rotate in response to rotation of the rotor 45. In some embodiments, a plurality of chambers 50 are attached to or mounted on the rotor 45; in the illustrated embodiment, four chambers 50 are present.

Figure 5A:
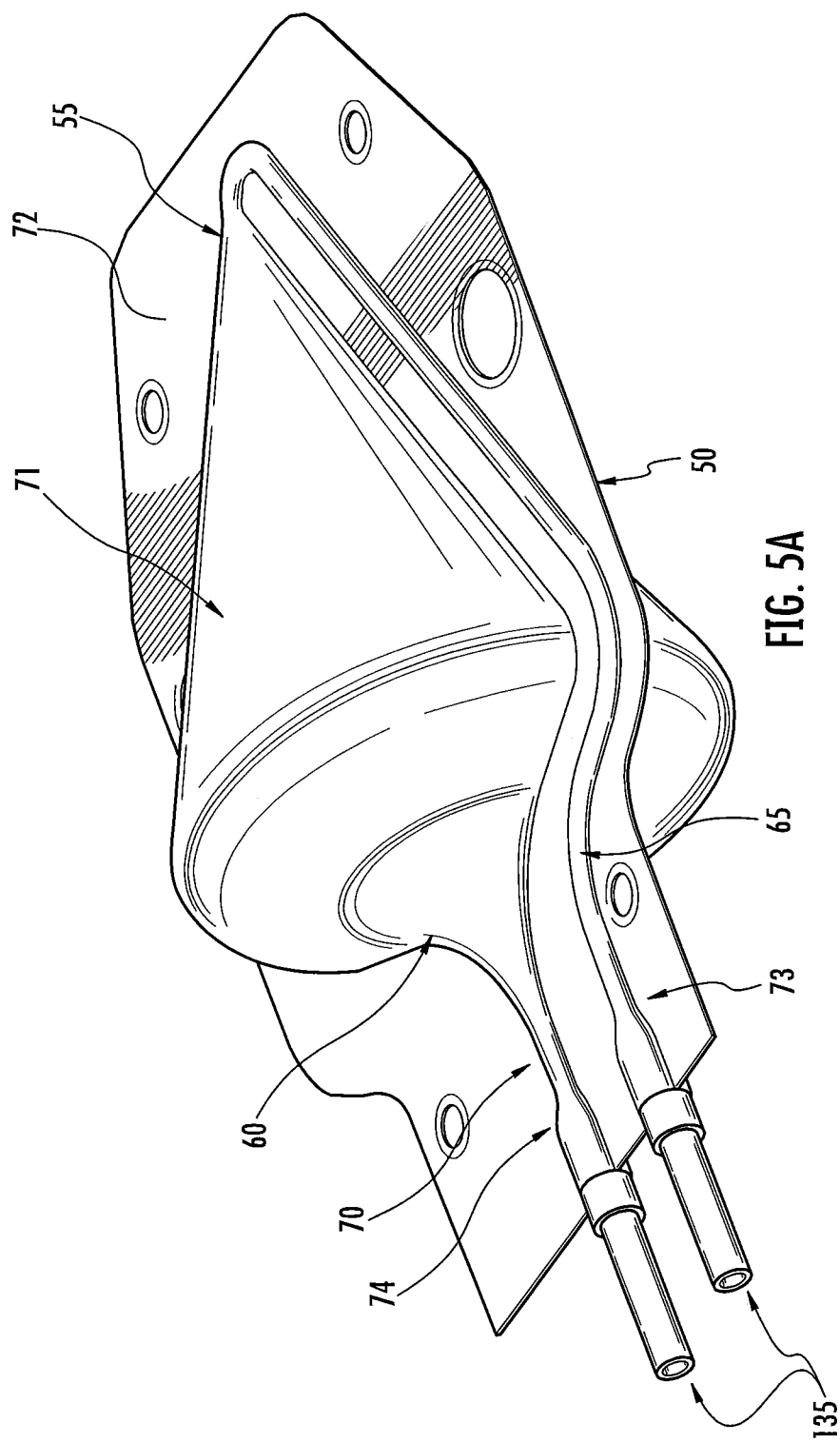
FIG. 5A illustrates a chamber for use in systems and assemblies according to some embodiments of the present invention.

An exemplary chamber 50 is illustrated in more detail in FIG. 5A. The chamber 50 may be substantially cone-shaped or may include a substantially cone-shaped portion, as illustrated, although other shapes are contemplated including, for example, cylindrical, rectangular, frustoconical, pyramidal, etc. The chamber 50 includes an inlet 55 and an outlet 60. The chamber 50 is typically attached to or mounted on the rotor 45 such that inlet 55 is situated toward the outer periphery of the rotor 45, and the outlet 60 is typically situated toward the center of the rotor 45 (see FIG. 6). The chamber 50 may be mounted on the rotor 45 such that the inlet 55 is situated proximate the outer periphery of the rotor 45 and the outlet 60 is situated proximate an inner radial portion of the rotor 45. The chamber 50 is configured to allow fluid flow therethrough while the rotor 45 and the chamber 50 rotate about an axis. The force of fluid flowing from the inlet 55 to the outlet 60 can substantially oppose a centrifugal force created by the rotation of the rotor 45 and the chamber 50. In this regard, particles can be substantially immobilized in the chamber 50, such as in a fluidized bed in the chamber 50, by use of the summation of forces acting on the particles. This action is described in more detail in U.S. Pat. Nos. 5,622,819; 5,821,116; 6,133,019; 6,214,617; 6,334,842; 6,514,189; 6,660,509; 6,703,217; 6,916,652; 6,942,804; 7,029,430; and 7,347,943; and U.S. Patent Application Publication Nos. 2005/0266548 and 2008/0264865, the disclosure of each of which is hereby incorporated by reference in its entirety.

In some embodiments of the present invention, and as illustrated in the figures, the rotor 45 may rotate in a plane substantially coaxial with the gravitational axis (i.e., the rotor may rotate about a substantially horizontal axis). Particles are substantially immobilized within a fluidized bed within the chamber 50 by use of the summation of the vector forces acting on each particle. Embodiments of such apparatus have been disclosed in U.S. Pat. Nos. 5,622,819; 5,821,116; 6,133,019; 6,214,617; 6,660,509; 6,703,217; 6,916,652; 6,942,804; 7,347,943; and U.S. Patent Application Publication Nos. 2005/0266548 and 2008/0264865, the disclosure of each of which is hereby incorporated by reference in its entirety. Though cells and particles are light in weight, their mass is non-zero. Consequently, gravity has a significant effect on the suspended particle or cell, and this effect will increase with time. The weight of the suspended particles or cells causes these particles to settle to the lowest regions of the container, disrupting the balance of forces which initially suspended them in the chamber. As is seen in prior art devices, particles tend to aggregate and the aggregation of these particles into a larger particle results in an increased centrifugal effect which causes the aggregates to migrate to longer radii, eventually causing destabilization of the fluidized bed.

In some other embodiments of the present invention, the rotor 45 may rotate in a plane substantially transverse to the gravitational axis. In this regard, the rotor 45 may rotate about a substantially vertical axis. Embodiments of such apparatus have been disclosed in U.S. Pat. Nos. 4,939,087; 5,674,173; 5,722,926; 6,051,146; 6,071,422; 6,334,842; 6,354,986; 6,514,189; 7,029,430; 7,201,848; and 7,422,693, the disclosure of each of which is hereby incorporated by reference in its entirety. Particles are substantially immobilized within a fluidized bed within the chamber 50 by use of the summation of the vector forces acting on each particle. More particularly, the flow of liquid media acts to create a force which opposes the centrifugal force field created by the rotating chamber(s).

In still other embodiments, the rotor may rotate about any axis between a horizontal axis and a vertical axis, including, for example, a substantially horizontal axis.

Referring again to FIG. 5A, the chamber 50 may include a substantially conical body portion 71, and a flange 72 that surrounds at least a portion of the conical body portion 71 and/or that extends about at least a portion of a perimeter of the conical body portion 71 (e.g., the flange 72 defines a plane that "wraps around" at least a portion of the chamber 50 and/or the conical body portion 71). The chamber inlet 55 may be at an apex of the conical body portion 71. The chamber outlet 60 may be proximate a base of the conical body portion 71. As illustrated, the chamber 50 includes inlet and outlet fluid paths 65, 70 which may be integrated with the flange 72 of the chamber 50. The inlet fluid path 65 may be external to the conical body portion 71 and may extend around at least a portion of the perimeter of the conical body portion 71. As described in more detail below, tubes may connect with the flange inlet and outlet fluid paths 65, 70. In these embodiments, the flange inlet and outlet fluid paths 65, 70 may include substantially parallel segments 73, 74 extending from the point at which the tubes connect with the flange inlet and outlet fluid paths 65, 70.

Figure 5B:
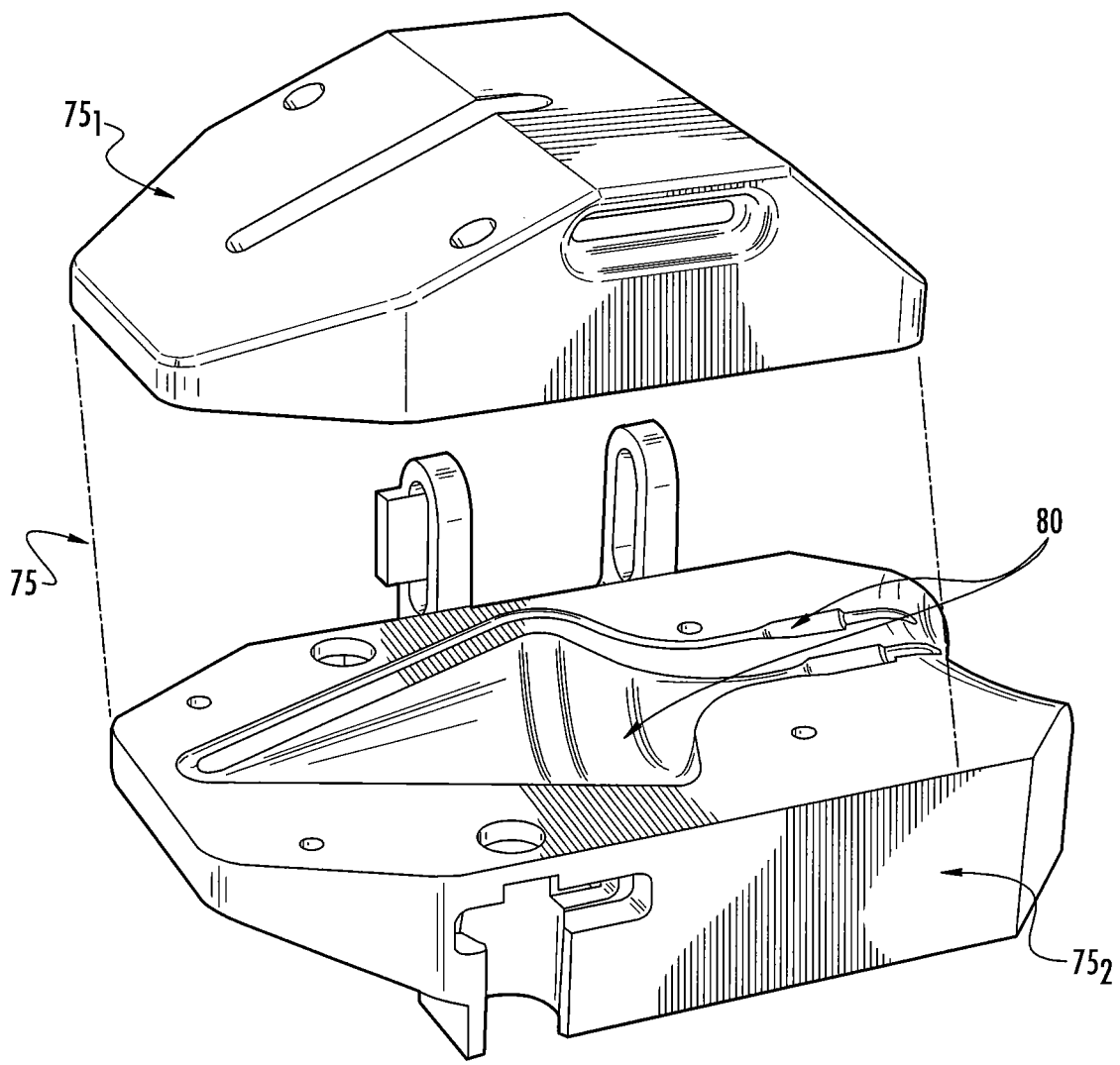
FIG. 5B illustrates a chamber holder for use in systems and assemblies according to some embodiments of the present invention.
Figure 7:
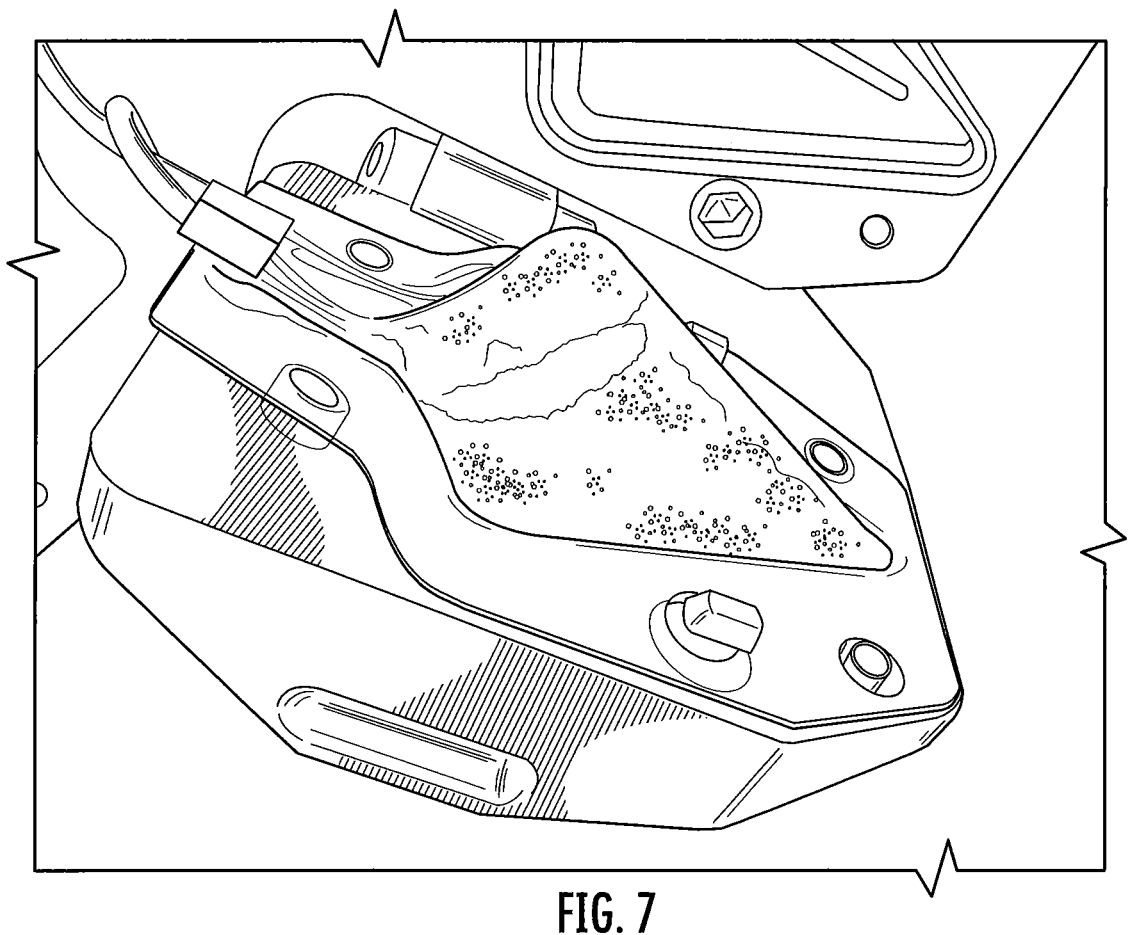
FIG. 7 is a top perspective view of a disposable chamber according to some embodiments of the present invention.

The chamber 50 may fit within a holder, such as the chamber holder 75 illustrated in FIG. 5B. The chamber holder 75 can carry all or a significant portion of centripetal forces on the chamber 50. In some embodiments, the chamber 50 (which may include the inlet and outlet paths 65, 70) may be disposable, as will be described in more detail below. In some embodiments, such as illustrated in FIG. 7, the chamber 50 is disposable and made of a polymeric material which may be flexible (e.g., a "bag chamber"). Therefore, the chamber holder 75 may be particularly useful where the chamber 50 is disposable, as the chamber 50 (on its own) may not be able to take the loads experienced when the rotor 45 and chamber 50 is rotating, especially at high speeds and/or for a long period of time. The chamber holder 75 can have increased rigidity or strength relative to the chamber 50.

Figure 6:
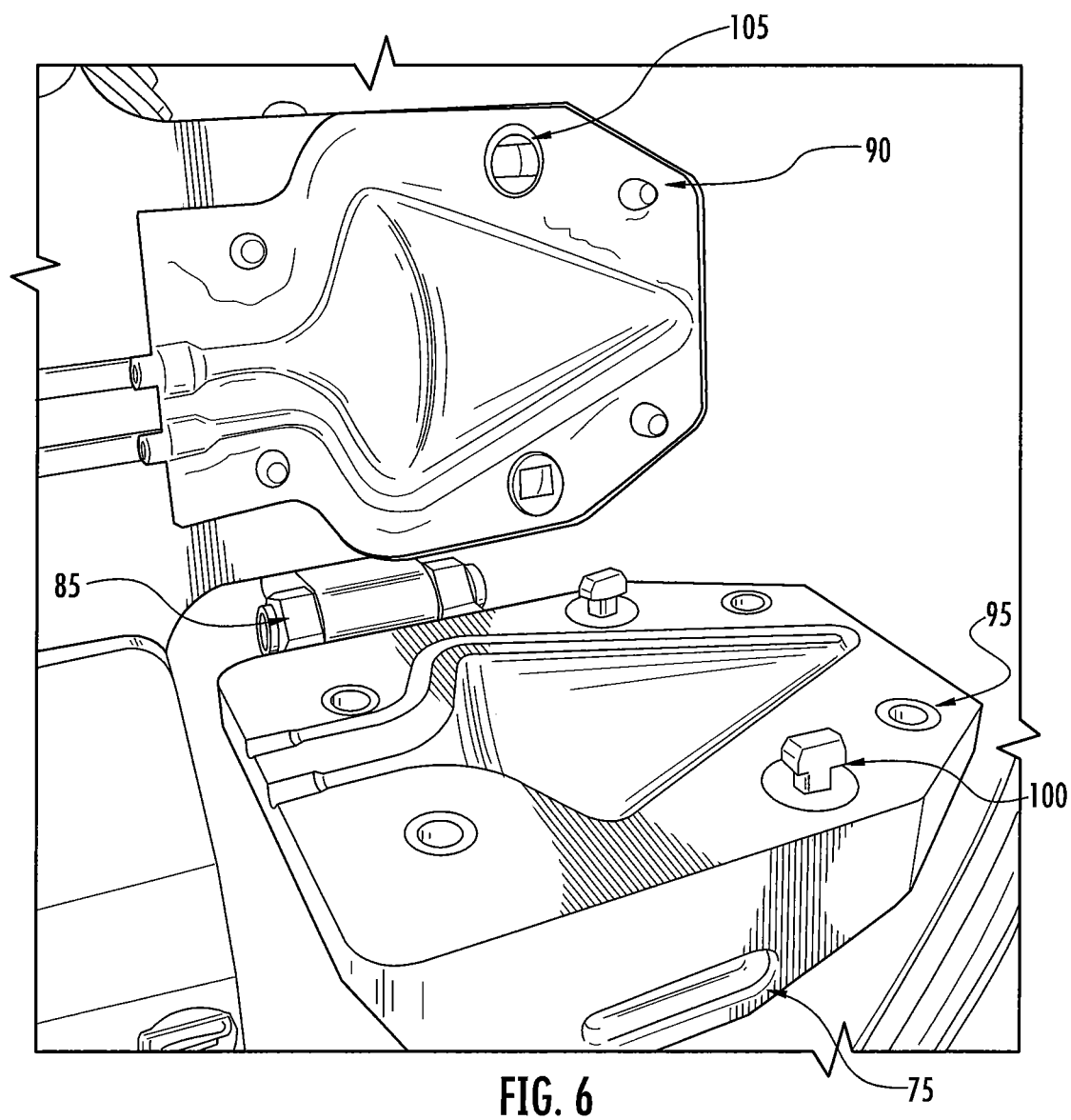
FIG. 6 illustrates a chamber and chamber holder in position in the system of FIG. 1 according to some embodiments of the present invention.

The chamber holder 75 includes cavities 80 sized to matably receive the chamber 50 and the associated inlet and outlet paths 65, 70 (where used) when the chamber holder 75 holds the chamber 50. Turning to FIGS. 6 and 7, the chamber holder 75 and/or the rotor 45 may include a hinge assembly 85 located on or near the rotor 45 such that the chamber holder 75 can be rotated to open and close over or under the chamber 50. In this regard, the chamber holder(s) 75 may be configured to releasably enclose the chamber(s) 50. At least one locating pin 90 may be located on or near the rotor 45, with the pin(s) 90 configured to mate with corresponding aperture(s) 95 in the chamber holder 75. In some embodiments, the pin(s) 90 can be located on the chamber holder 75 and the corresponding apertures 95 can be located on or near the rotor 45. The chamber holder 75 may also include at least one lock 100 configured to mate with corresponding aperture(s) 105 located on or near the rotor 45. In some embodiments, the lock(s) 100 may be on or near the rotor 45 and the corresponding aperture(s) 105 may be located on the chamber holder 75. Referring back to FIG. 5B, the chamber holder 75 may include a top shell $75_1$ and a bottom shell $75_2$. In some embodiments, the bottom shell $75_2$ may be mounted to or integrated with the rotor 45 and the top shell $75_1$ may be configured to open and close. In other embodiments, the top shell $75_1$ may be mounted to or integrated with the rotor 45 and the bottom shell $75_2$ may be configured to open and close. In these embodiments, the pin(s) 90, aperture(s) 95, and/or lock(s) 100 may be located on either the top shell $75_1$ or the bottom shell $75_2$.

Referring back to FIGS. 3 and 4, at least one chamber 50 may be attached to or mounted on or held by the rotor 45. In the illustrated embodiment, four chambers 50 are attached to or mounted on the rotor 45. In other embodiments, any number of chambers 50 may be attached to or mounted on the rotor 45. Also, in the illustrated embodiment, a chamber holder 75 has been rotated closed to cover each of the chambers 50. The chamber holders 75 may include a window 110, which may allow an operator to view or allow visual access to the interior of the chamber 50. Although shown as two pieces 75$_1$, 75$_2$ in FIG. 5B, the chamber holder 75 may comprise a single piece or more than two pieces to hold a respective chamber 50.

Figure 8:
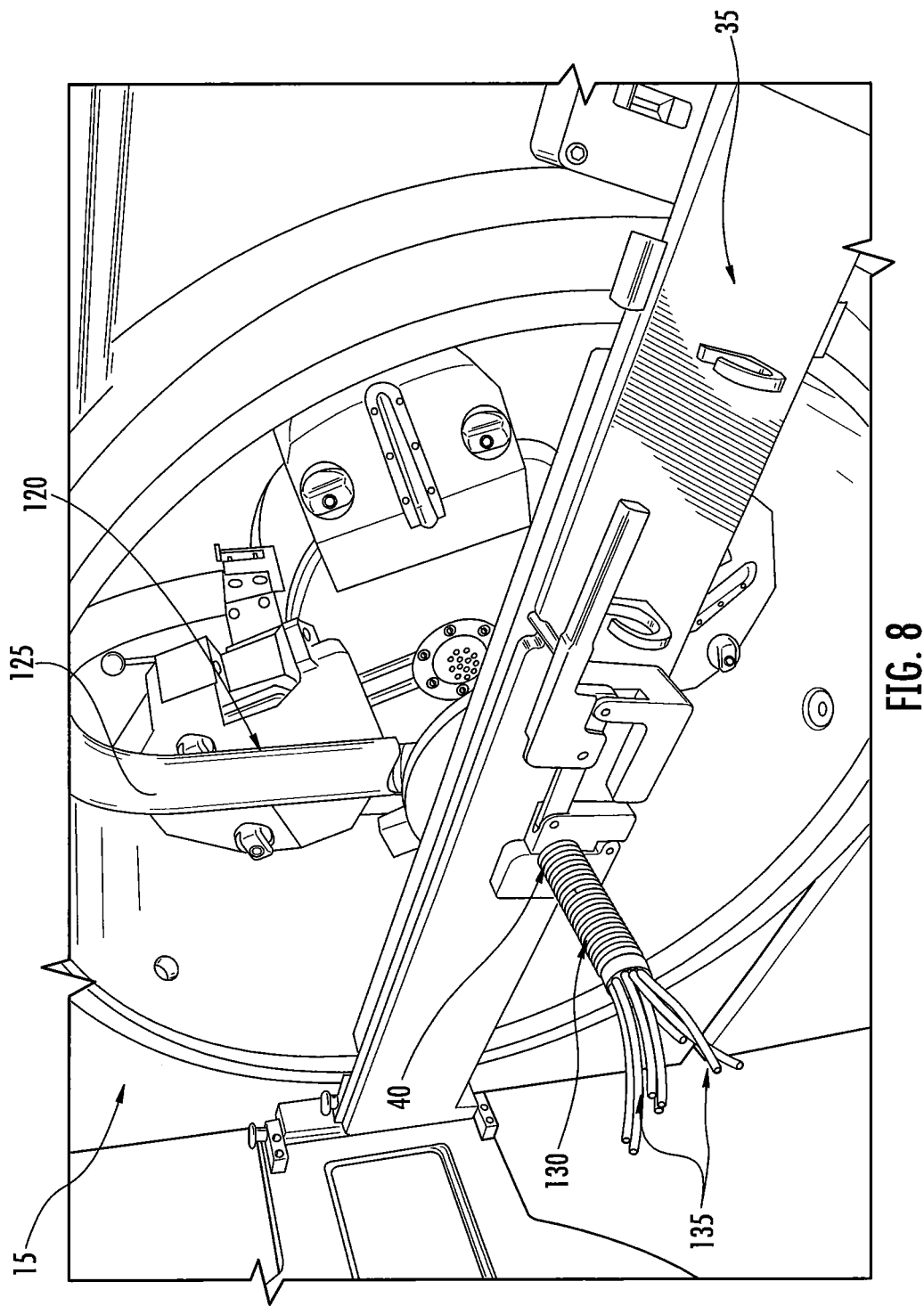
FIG. 8 is a perspective view of an umbilical assembly according to some embodiments of the present invention.

Turning to FIG. 8, at least a portion of an umbilical assembly 120 extends through the aperture 40 of the flange 35. The umbilical assembly 120 can include a curvilinear umbilical guide or guide tube 125, which curves around or extends about the outer periphery of the rotor 45 and enters into and/or connects to a drum at the rear side of the rotor 45, as described in more detail below. The guide 125 is typically constructed of a relatively strong material, such as aluminum or steel, to provide strength to the umbilical assembly 120 such that the umbilical assembly 120 can be "spun" about the same axis as the rotor 45, as described in more detail below. In various embodiments, the guide 125 may extend all the way through the aperture 40 of the flange 35, may extend to the aperture 40, or may terminate before reaching the aperture 40, as illustrated in FIG. 8.

Umbilical assemblies described herein may include a flexible conduit residing in the guide tube 120. First and second elongate channels or passageways for each chamber 50 extend through the conduit. The first channel or passageway is in fluid communication with the inlet 55 of a respective chamber 50 and the second channel or passageway is in fluid communication with the outlet 60 of the respective chamber 50. The channels or passageways (i.e., all the channels or passageways in the conduit) are preferably held in a spaced-apart relationship relative to one another, as will be described in more detail below. As used herein, the terms "channel" and "passageway" are interchangeable in this context.

As illustrated in FIG. 8, for example, the umbilical assembly 120 can include a flexible conduit 130 mounted within and extending along the length of the umbilical guide 125. In other words, the conduit 130 can reside within the umbilical guide or guide tube 125. The conduit 130 may comprise a convoluted tube which provides suitable flexibility to bending and can also have high torsional rigidity or strength. The conduit 130 preferably has a sufficiently long fatigue life that can withstand continual flexing associated with centrifugal operation; an exemplary conduit 130 is type FPI available from Flexicon Limited, Birmingham, England, constructed of a modified Polyamide 12. The conduit 130 may be corrugated flexible conduit. The conduit 130 may have any inside diameter and any outside diameter suitable to accommodate the other components of the umbilical assembly 120, described below. In some embodiments, the conduit 130 may have inside diameter of about 35.5 millimeters and an outside diameter of about 42.5 millimeters. In some embodiments, grease or another lubricous material is provided between the umbilical guide 125 and the conduit 130 to reduce friction therebetween.

The aforementioned channels or passageways of the umbilical assembly 120 can be or include first and second flexible tubes 135 for each chamber 50. The tubes 135 may be constructed of any flexible material such as any flexible polymer including, but not limited to, PVC. The tubes 135 are mounted within and extend along the length of the conduit 130. One of the tubes 135 of each chamber 50 can connect with the inlet 55 of the chamber 50 (or, where used, the inlet path 65 of the chamber 50) and the other can connect with the outlet 60 of the chamber 50 (or, where used, the outlet path 70 of the chamber 50) (see FIG. 5A). In the illustrated embodiments, umbilical assembly 120 includes eight flexible tubes 135, wherein two of the tubes 135 connect with each of the four chambers 50. The conduit 130 and the tubes 135 extend through the aperture 40 of the flange 35, regardless of whether the umbilical guide 125 extends that far. In other words, the flexible conduit 130 and the tubes 135 therein extend from a location that is external to the enclosure or housing 15, through the access aperture 40, and into the internal cavity 44. The tubes 135 may have any inner diameter and any outer diameter suitable to fit an appropriate number of tubes 135 within the conduit 130, which may also include potting material therein, as described in more detail below. In some embodiments, the tubes 135 may have an inner diameter of about ¼ inch and an outer diameter of about ⅜ inch (e.g., where the conduit 130 has the dimensions described above, and where eight tubes 135 are employed).

Figure 9A:
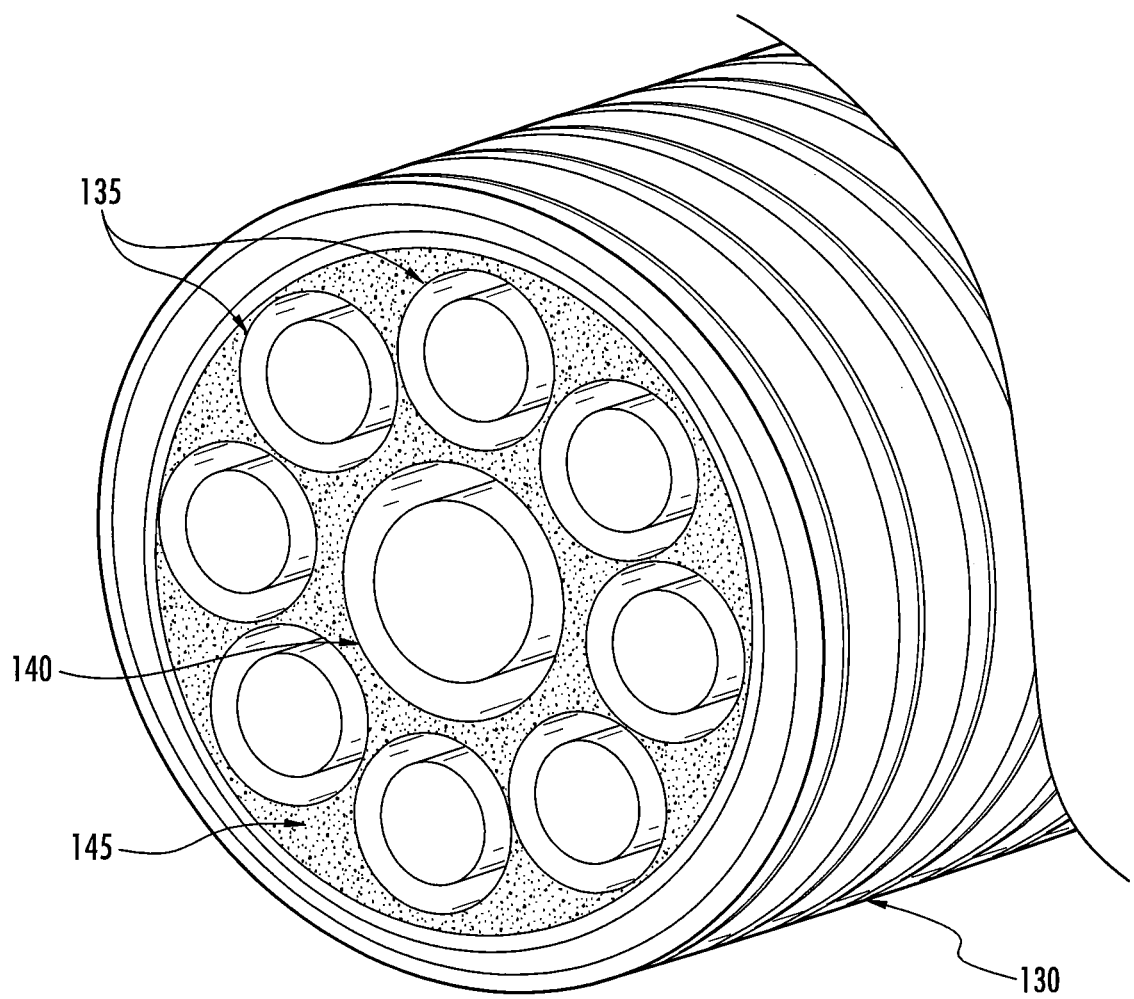
FIG. 9A is cross-sectional view of a portion of an umbilical assembly according to some embodiments of the present invention.

Referring to FIGS. 9A and 9B, in some embodiments, the umbilical assembly 120 includes a flexible center member 140 mounted within and extending along the length of the conduit 130. The flexible member 140 extends substantially along a centerline of the conduit 130, and the flexible tubes 135 form an array and surround the flexible member 140. The flexible member 140 may comprise a "dummy tube," similar to the tubes 135, but not in fluid communication with any of the chambers 50. In other embodiments, the flexible member 140 may be a tube with an open cavity having the same or smaller or larger diameter than the tubes 135, or may be solid tube, for example of polymeric material. For example, the flexible member 140 may comprise a tube having an inner diameter of about ⅜ inch and an outer diameter of about 9/16 inch, and the tubes 135 may have an inner diameter of about ¼ inch and an outer diameter of about ⅜ inch. Where the flexible member 140 comprises a tube, the inside of the tube may include potting material, as described in more detail below. In some other embodiments, the flexible member 140 comprises a tube configured to have fluid flow through the tube. The fluid may provide additional cooling to the umbilical assembly 120, for example.

The umbilical assembly 120 may also include potting material 145 within the conduit 130. The potting material 145 can separate the tubes 135 from the conduit 130, can separate the tubes 135 from each other, and/or can separate the tubes from the flexible member 140, where used. More specifically, the potting material 145 may be configured to hold the tubes 135 in a spaced-apart relationship relative to one another and/or hold the tubes 135 in a spaced-apart relationship relative to the conduit 130 and/or hold the tubes 135 in a spaced-apart relationship relative to the flexible member 140, where used. The potting material 145 can be useful in restricting movement (e.g., twisting) of the tubes 135 relative to one another during operation, as described in more detail below. In other words, the potting material 145 can "lock" the tubes 135 and/or the conduit 130 together so that the tubes 135 are inhibited from moving relative to one another and/or relative to the conduit 130. As used herein, "potting material" includes any solid flexible material that substantially fills the internal volume of the conduit and surrounds the tubes and/or flexible center member. The potting material 145 can be any suitable material, including a polymer such as polyurethane, for example. An exemplary potting material is F-25 flexible polyurethane, available from BJB Enterprises, Inc., Tustin, Calif.

As will be discussed in more detail below, the conduit 130 has opposite proximal and distal ends 130$_1$, 130$_2$. In some embodiments, the proximal end 130$_1$ of the conduit 130 and the tubes 135 contained therein extend through the access aperture 40. As illustrated in FIG. 9B, the proximal end 130$_1$ of the conduit 130 may include a flange 132 through which the tubes 135 extend. Where potting material is employed, the flange 132 may assist in housing the potting material in the conduit 130. The flange 132 may also assist in proper positioning of the conduit 130 with the tubes 135 contained therein. For example, the flange 132 may be situated on the outside of the aperture 40 (e.g., on the outside of the enclosure 15); the flange 132 may therefore allow an operator to position the proper length of conduit 130 in the interior cavity 44.

Figure 10:
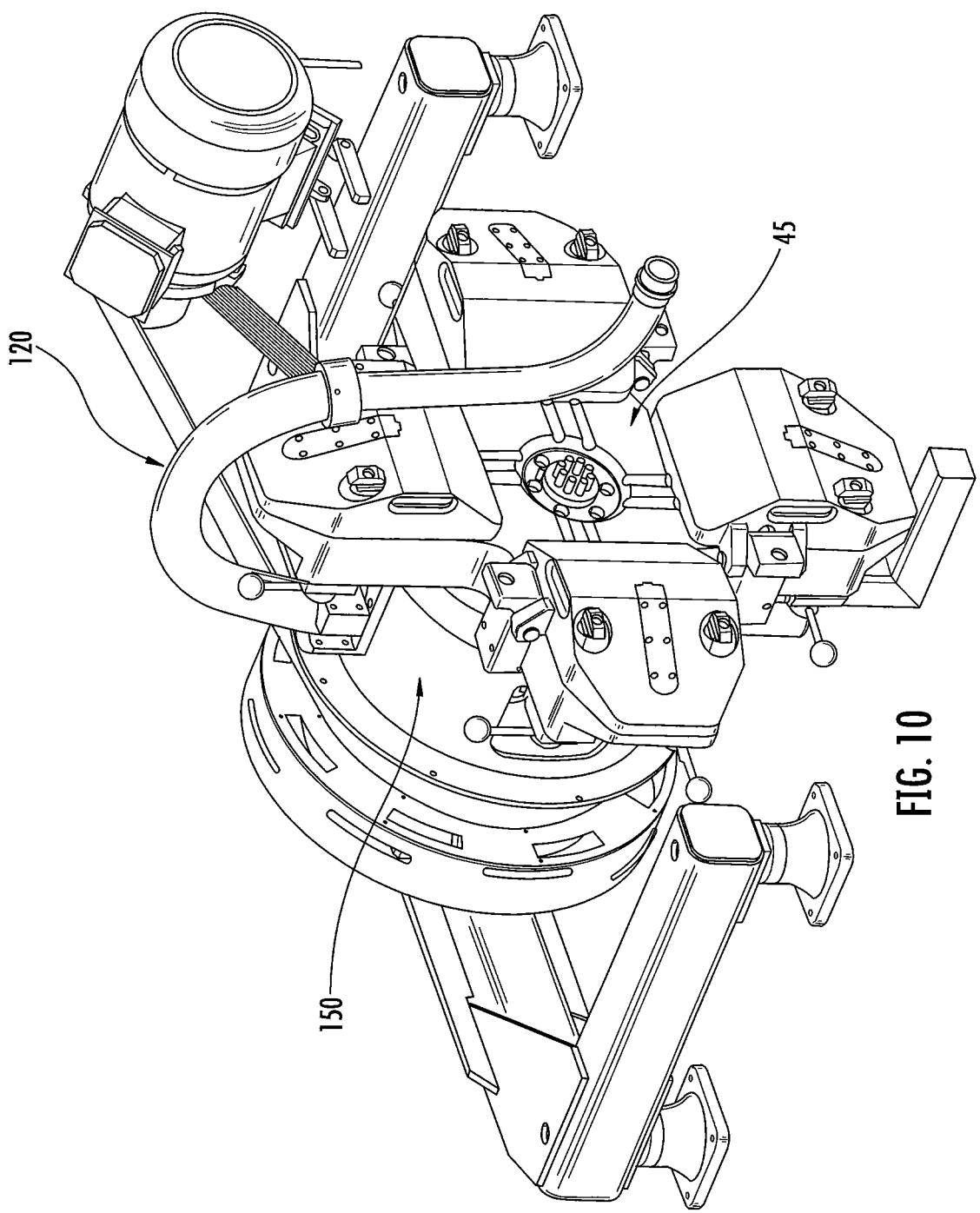
FIG. 10 is a perspective view of an umbilical assembly according to some embodiments of the present invention.
Figure 11:
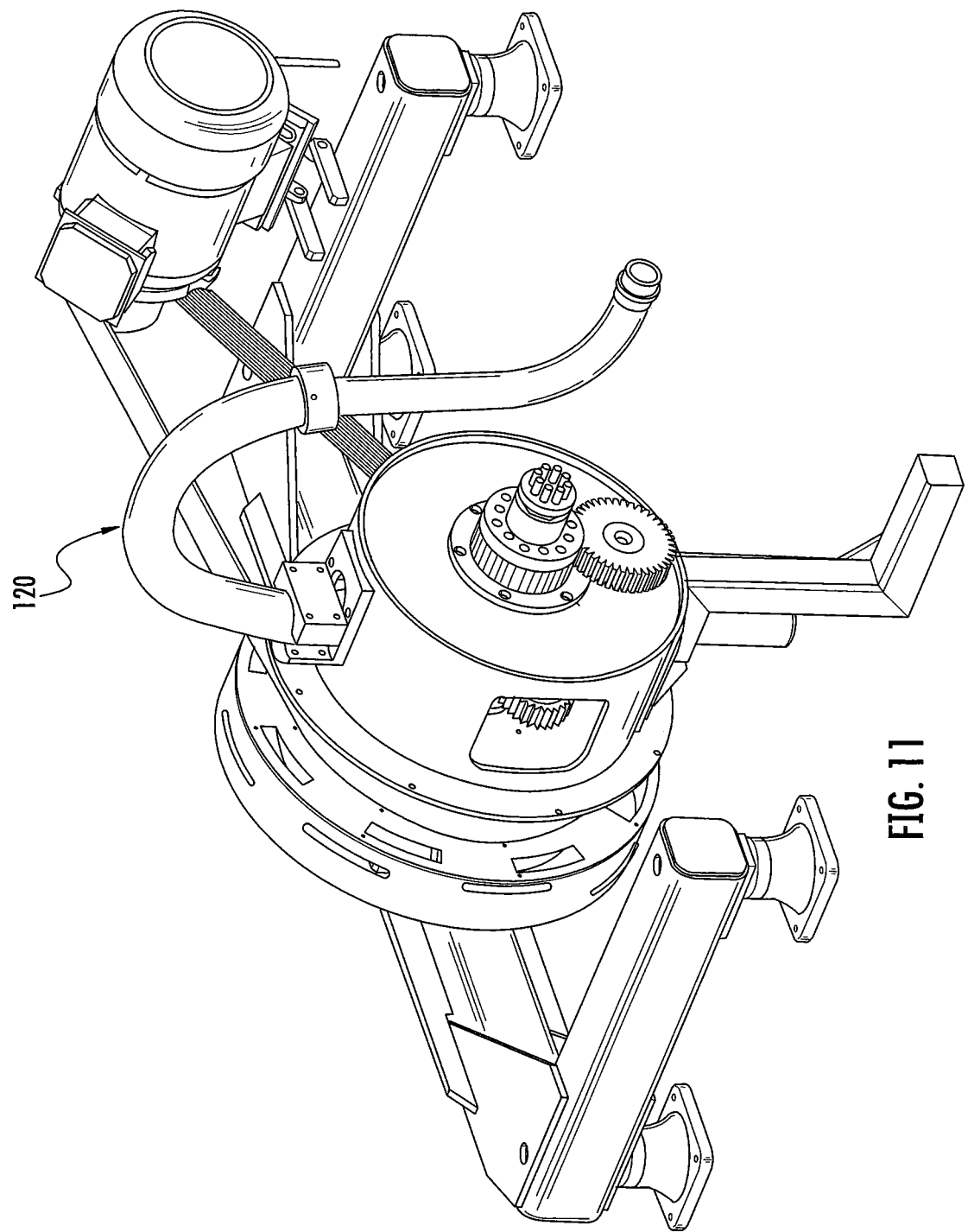
FIG. 11 is a perspective view illustrating the umbilical assembly of FIG. 10 connecting with a drum.
Figure 12:
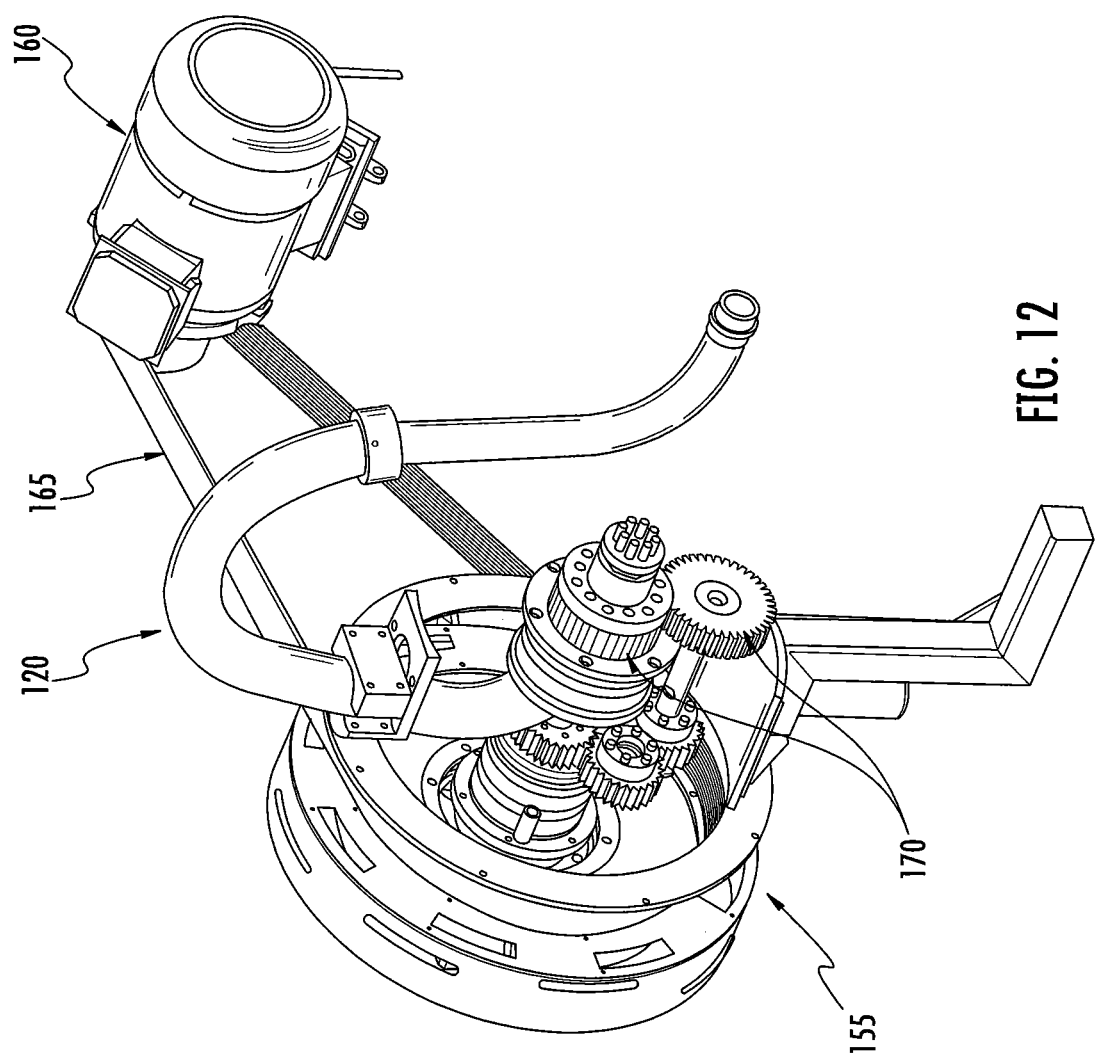
FIG. 12 is a perspective view illustrating a drive mechanism associated with the umbilical assembly of FIG. 10.

Referring now to FIGS. 10-12, the umbilical assembly 120 curves around or extends about the outer periphery of the rotor 45 and enters a drum 150 at the rear side of the rotor 45. In some embodiments, a portion of the umbilical assembly 120 connects with the drum 150. In the illustrated embodiment, a drive mechanism 155 is driven by a motor 160 and a belt 165. The drive mechanism 155 may include various gears 170, at least some of which may be located within the drum 150. In particular embodiments, the drive mechanism 155 causes the umbilical assembly 120 to rotate about an axis at speed X, and causes the rotor 45 to rotate about the same axis at speed 2X or about speed 2X. In other words, the umbilical assembly 120 rotates at one-half or about one-half the speed of the rotor 45. In some embodiments, the drum 150 is driven at speed X by the motor 160 (the umbilical assembly 120 in turn rotates at speed X), and the drive mechanism 155 includes gearing which causes the rotor 45 to rotate at speed 2X or about speed 2X.

Figure 13:
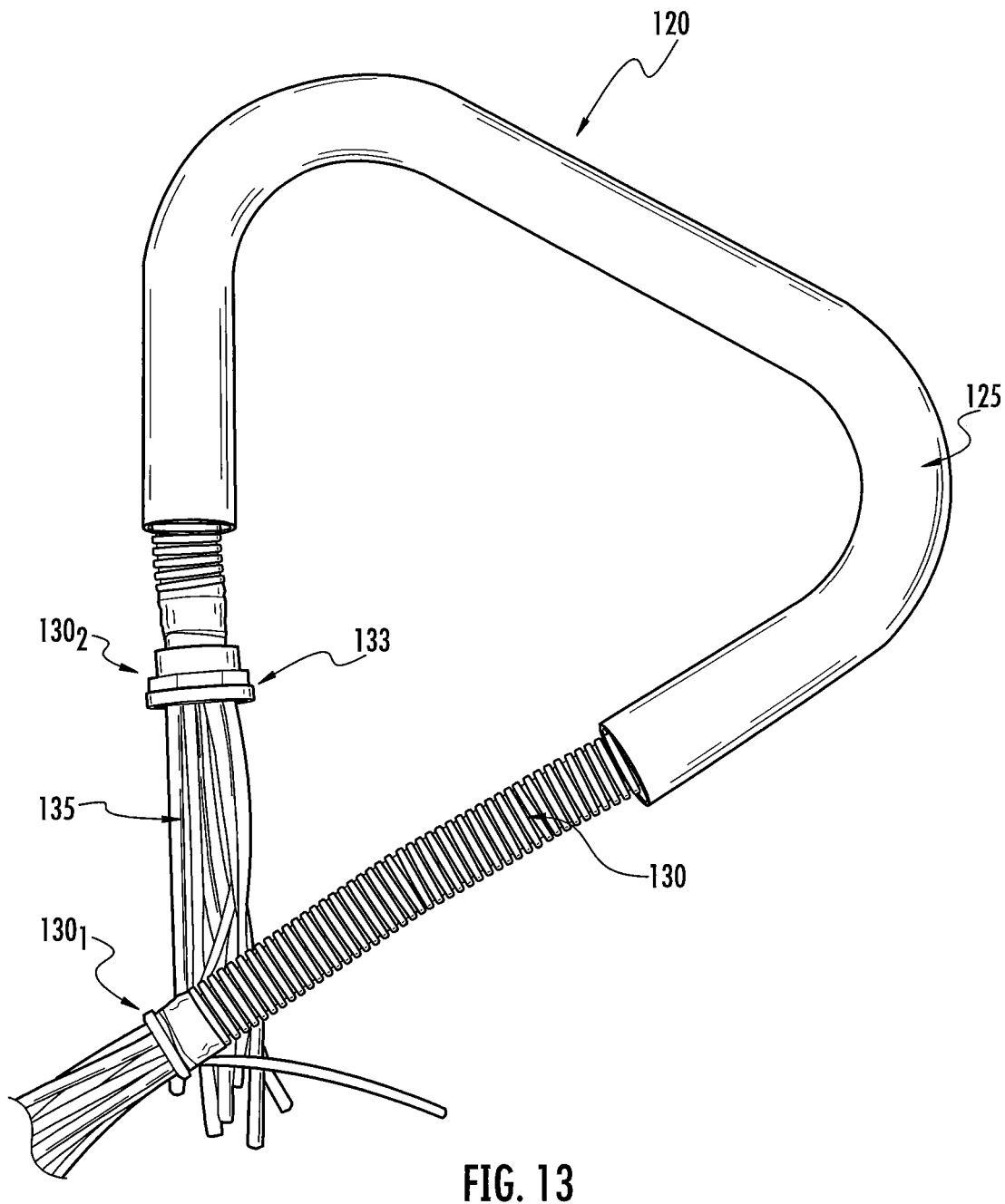
FIG. 13 is a top view of an umbilical assembly according to some embodiments of the present invention.
Figure 14A:
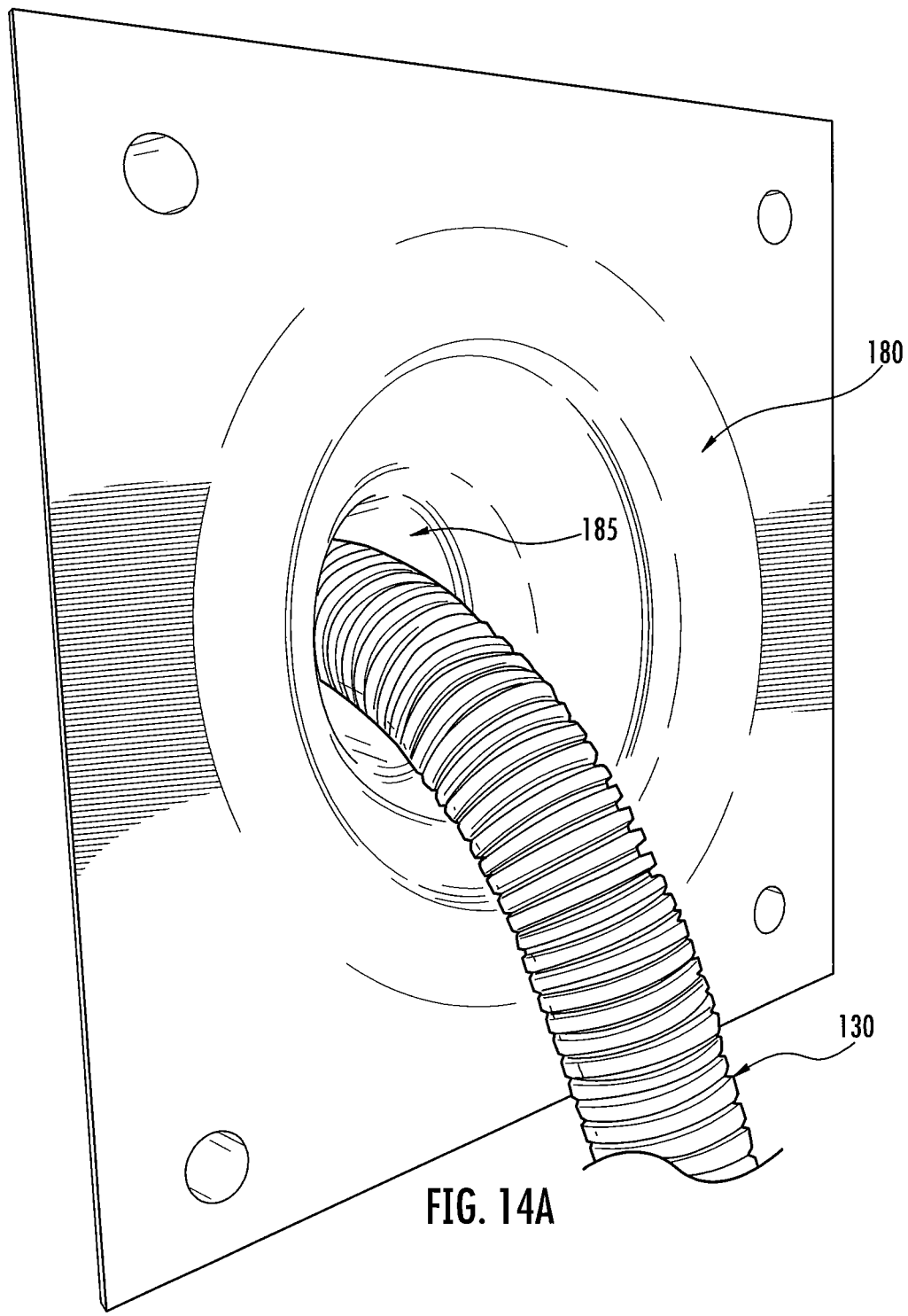
FIG. 14A is a perspective view of a funnel-shaped ingress/egress port for use with an umbilical assembly according to some embodiments of the present invention.
Figure 14C:
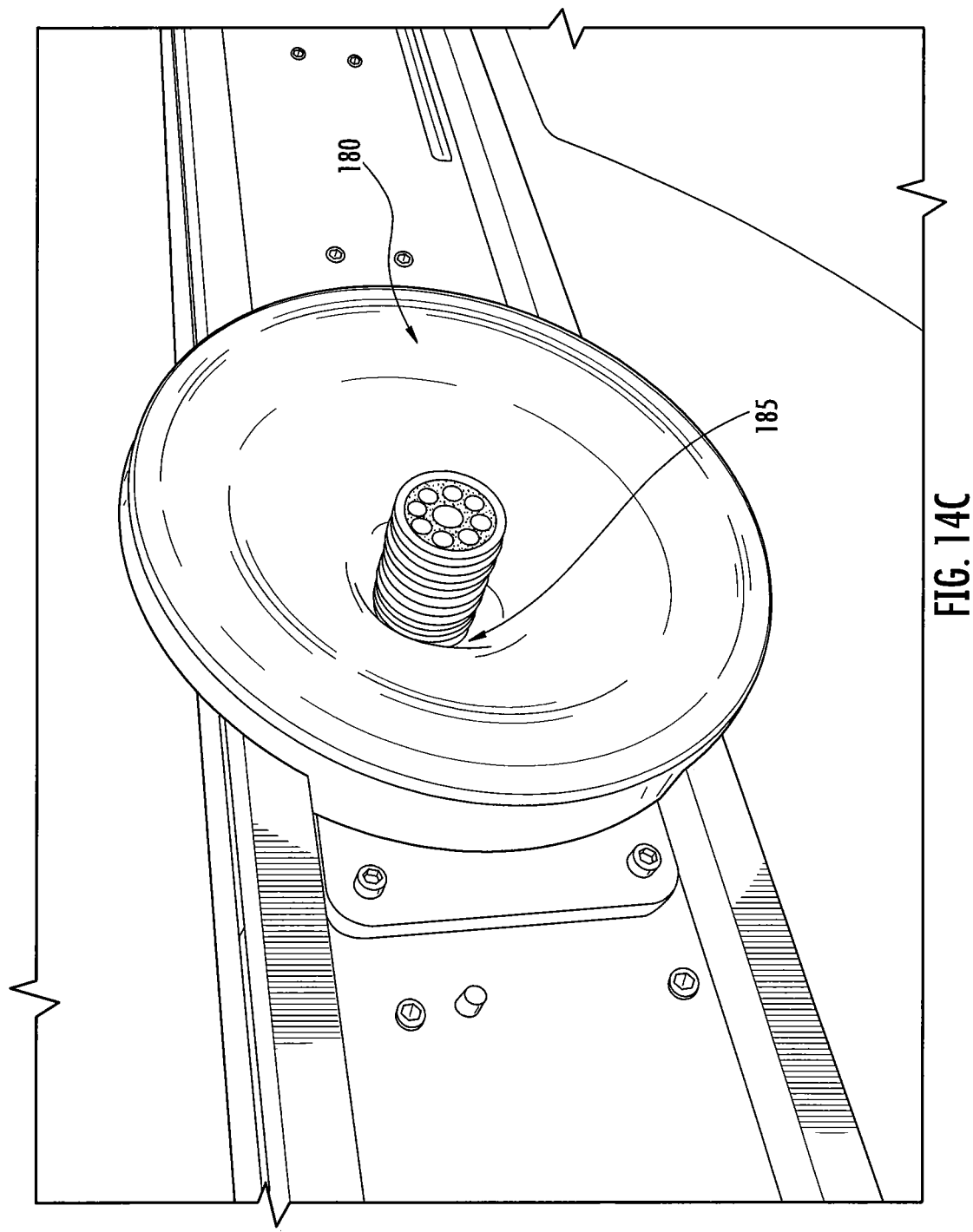
FIG. 14C is a perspective view of a funnel-shaped ingress/egress port for use with an umbilical assembly according to some embodiments of the present invention.
Figure 14D:
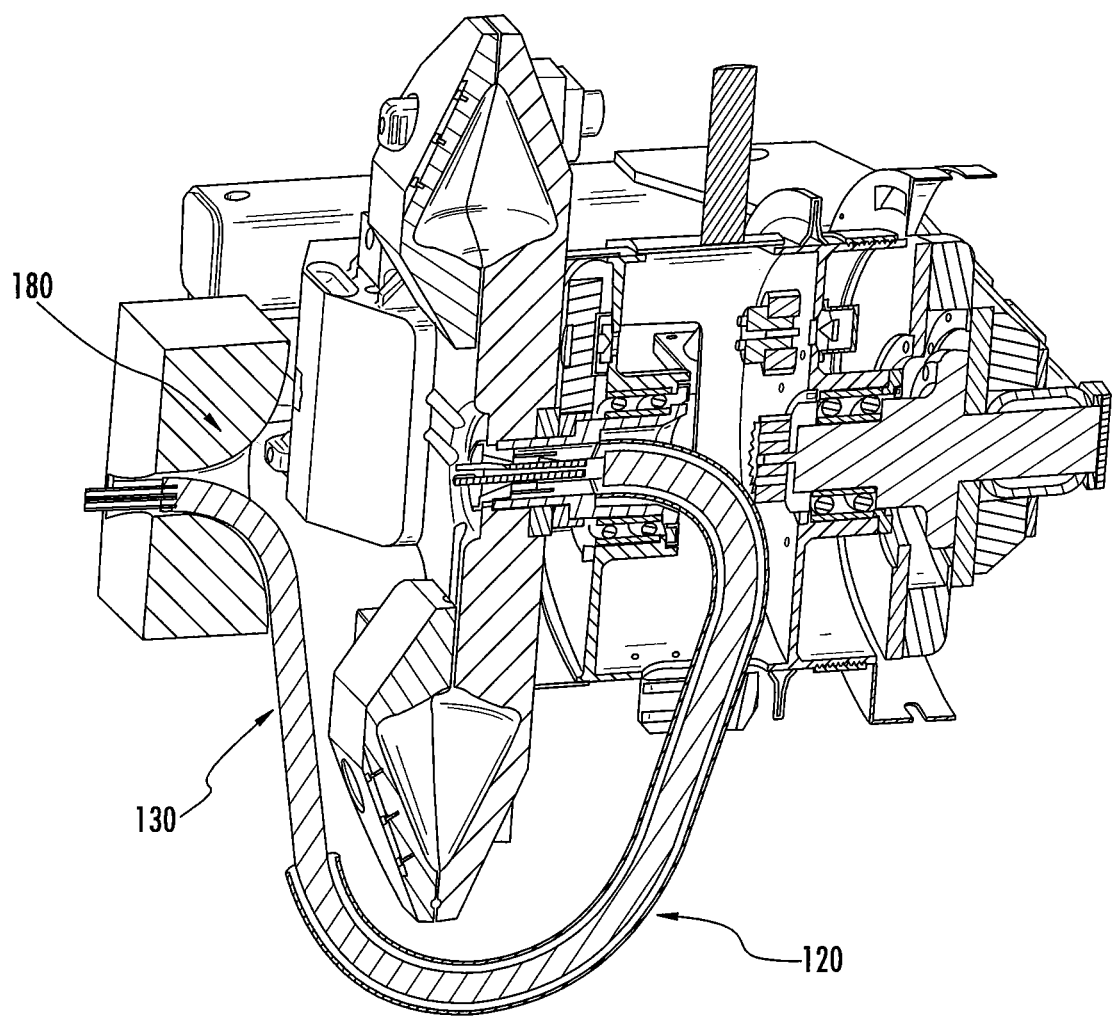
FIG. 14D illustrates a funnel-shaped ingress/egress port for use with an umbilical assembly according to some embodiments of the present invention.

FIG. 13 illustrates an exemplary arrangement and shape of the umbilical assembly 120. The conduit 130 has opposite proximal and distal ends $130_1$, $130_2$. In some embodiments, the proximal end $130_1$ of the conduit 130 and the tubes 135 contained therein extend through the access aperture 40 (see FIGS. 15 and 16, for example). The distal end $130_2$ of the conduit 130 extends through the drum 150 and may connect to the rotor 45 to thereby allow the tubes 135 to be fluidly connected with the chambers 50. In some embodiments, and as illustrated, the conduit distal end $130_2$ includes a coupling 133. The coupling 133 can couple the conduit 130 to the rotor 45 and therefore allow the tubes 135 to be fluidly connected with the chambers 50. In some embodiments, the coupling 133 has a hexagonal shape, although other shapes are contemplated, including other polygonal shapes.

In this configuration, the coaxial half-speed rotation of the umbilical assembly 120 inhibits the tubes 135 of the umbilical assembly 120 from being completely twisted during rotation of the rotor 45. The complete scientific explanation for this phenomenon can be found in, for example, U.S. Pat. No. 3,586,413 to Adams, the disclosure of which is hereby incorporated by reference herein in its entirety. To summarize, if the rotor 45 has completed a first 360° rotation and the umbilical assembly 120 a 180° half-rotation in the same direction, the tubes 135 of the umbilical assembly 120 will be subjected to a 180° twist in one direction. Continued rotation of the rotor 45 for an additional 360° and umbilical assembly 120 for an additional 180° will result in the tubes 135 of the umbilical assembly 120 being twisted 180° in the other direction, returning the tubes 135 to their original untwisted condition. Thus, the tubes 135 of the umbilical assembly 120 may be subjected to a continuous partial twist or flexure or bending during operation but are never completely rotated or twisted about their own axis.

This solution can provide advantages over typical continuous flow centrifuges. In conventional mechanisms, when a length of tubing is fixedly attached to the rotation axis of a device which contains the fluid material to be centrifuged, the entire length of tubing must be rotated by use of rotating seals or other means to avoid twisting the tubing. However, these seals too frequently become the source of leaks and/or contamination.

In contrast, the umbilical assembly 120 of the present invention provides a transition from the "rotating world," including the rotor 45, to the "stationary world," such as that area outside the enclosure 15. Rotary unions and seals are not required, providing a sterile and completely closed system. Other advantages can include the use of disposable components that can be easily replaced, resulting in sterile paths, as described in more detail below.

Umbilical-like arrangements for use with continuous flow centrifuges have been disclosed in, for example, U.S. Pat. Nos. 4,216,770, 4,419,089, 4,389,206, and 5,665,048. However, these solutions do not adequately address the high stresses and strains imparted on the tubes due to the g-forces created by rotating the centrifuge at high speeds and/or due to the continuous fluid flow necessary to substantially immobilize particles. Moreover, rotating the centrifuge at high speeds creates increased torque of the umbilical system and the tubes contained therein, and the arrangements disclosed to date do not allow the umbilical system and the tubes contained therein to be rotated at a high rate of speed for an acceptable amount of time before failing. In other words, it is believed that the aforementioned solutions simply do not allow the systems to be "scaled up" to an appreciable degree and do not allow the system to be rotated at high rates of speed without rapid and catastrophic failure of the tubing system. This is the case, at least in part, because the friction increases as the speed and the scale increase, producing an increased torque of the umbilical system.

The present invention addresses these deficiencies by providing a more robust umbilical assembly that can withstand higher rotational speeds (and therefore higher g-forces), allowing a system, such as a continuous flow centrifuge, to be "scaled up" to larger sizes without subjecting the umbilical assembly to immediate or rapid catastrophic failure. This is due to the configuration of the umbilical assemblies of the present invention, such as the umbilical assembly 120 illustrated in FIGS. 8-14.

In this configuration, excessive twisting of the tubes 135 is inhibited during operation (i.e., while the rotor is rotated about the axis at speed 2X and the umbilical assembly is rotated about the axis at speed X). More particularly, excessive twisting of the tubes 135 relative to one another and relative to the conduit 130 is prevented. Put another way, the tubes 135 and the conduit 130 are effectively "locked" together (e.g., by use of the potting material 145), thereby inhibiting relative movement of the components. In addition, excessive rubbing of tubes 135 against each other and against the conduit 130 is reduced, if not totally prevented. The result is a tubing system that can experience a relatively long life in a large-scale system that is rotated about the axis at a high rate of speed.

This is accomplished, in part, by restricting the movement of the tubes 135 within the conduit 130. The potting material 145 can maintain the tubes 135 in place, and thereby prevent the tubes 135 from excessive twisting relative to the conduit 130. In other words, the potting material 145 can "lock" the tubes 135 and/or the conduit 130 together, thereby inhibiting movement of the tubes 135 relative to one another and/or relative to the conduit 130. The potting material 145 can also provide a buffer between the individual tubes 135, thereby preventing the tubes 135 from rubbing against one another. Moreover, the potting material 145 can provide a buffer between the tubes 135 and the conduit 130, thereby preventing the tubes 135 from rubbing against the conduit 130 during operation. Rubbing of these components can not only cause continual stress, but can also generate heat, further weakening the components.

Moreover, where used, the flexible member 140 can serve to maintain the tubes 135 in an organized array around the flexible member 140, further reducing twisting of the tubes 135. Where potting material 145 is employed, the potting material 145 can serve to "lock" the conduit 130, the tubes 135, and/or the flexible member 140 together, thereby inhibiting movement of the components relative to one another. Moreover, the potting material 145 may serve as a buffer between the tubes 135 and the flexible member 140, thereby preventing the tubes 135 from rubbing against the flexible member during operation. Rubbing of these components can not only cause continual stress, but can also generate heat, further weakening the components.

Selection of an appropriate material for the conduit 130 can prevent failure thereof due to rubbing against the umbilical guide 125 during operation. Furthermore, grease or other lubricous material can be applied between the conduit 130 and the guide 125 to further reduce friction and potential failure of the conduit 130 and/or the tubes 135 during operation (e.g., fatigue failure of the conduit 130). Moreover, the inside of the guide 125 can be polished (e.g., mechanically polished) to further reduce friction between the conduit 130 and the guide 135. Additionally or alternatively, the inside of the guide 125 and/or the outside of the conduit 130 can be coated with a lubricous material, such as Teflon®, to reduce friction between the two components.

Using these configurations, a system, such as a continuous flow centrifuge without use of rotary seals or the like, has been successfully "scaled-up" as follows. The rotor and the chamber(s) can be rotated at speeds of at least 3000 RPM. This corresponds to a g-force of about 1000 g at the chamber (e.g., at ⅓ the height of the chamber "cone" or ⅓ chamber height from the "tip" of the chamber). The fluid flow rates through each chamber can be at least 1 liter/minute. Thus, where four chambers are employed, for example, the total flow rate can be at least 4 liters/minute. The volume of each chamber can be at least 1 liter. Thus, where four chambers are employed, for example, the total chamber volume can be at least 4 liters. Of course, lower rotational speeds, flow rates, and/or chamber volumes can be employed for various operations (e.g., the rotational speed of the rotor can range from 0-3000 RPM and/or the fluid flow rate through each chamber can range from 0-1 liters/minute and/or the volume of each chamber can be less than 1 liter). Moreover, it is believed that the aforementioned embodiments and the alternative embodiments disclosed below can allow for a robust system that is "scaled-up" to an even higher degree (e.g., rotational speeds higher than 3000 RPM, flow rates higher than 1 liter/minute per chamber, chamber volumes greater than 1 liter, etc.). More specifically, it is believed that the aforementioned embodiments and the alternative embodiments disclosed below can allow for a robust system that employs rotation speeds of about 10, 25, 50, 100, 250, 500, 750, 1000, 1250, 1500, 1750, 2000, 2500, 3000, 5000, or 10,000 RPM or more or any subrange therein; it is also believed that the aforementioned embodiments and the alternative embodiments disclosed below can allow for a robust system that can produce and withstand g-forces of about 10, 25, 50, 100, 250, 500, 750, 1000, 1250, 1500, 1750, 2000, 2500, 3000, 5000, or 10,000 g or more or any subrange therein. Likewise, it is believed that the aforementioned embodiments and the alternative embodiments disclosed below can allow for fluid flow rates of about 0.0001, 0.001, 0.01, 0.1, 0.25, 0.5, 0.75, 1, 1.25, 1.5, 1.75, 2, 2.5, 3, 5, 10, 20, 25, or 50 liters/minute per chamber or more or any subrange therein; it is also believed that the aforementioned embodiments and the alternative embodiments disclosed below can allow for individual chamber volumes of about 0.0001, 0.001, 0.01, 0.1, 0.25, 0.5, 0.75, 1, 1.25, 1.5, 1.75, 2, 2.5, 3, 5, 10, 20, 25, or 50 liters or more or any subrange therein.

Other embodiments of the umbilical assembly 120 are contemplated. For example, the flexible member along the centerline of the conduit can be omitted. One of the tubes may extend substantially along a centerline of the conduit, with the remaining tubes forming an array and surrounding the center tube. In this regard, the center tube takes the place of the "dummy tube," and it connects with either the inlet or outlet path of one of the chambers. Potting material may be provided to prevent twisting and rubbing, as described in more detail above.

In still other embodiments, potting material is not required. For example, the umbilical assembly could comprise one solid extrusion with a plurality of channels or passageways extending therethrough. Each channel or passageway would connect with either an inlet or an outlet of one of the chambers. The solid extrusion may be flexible, and may be contained within a guide to provide strength, such as the guide 120 described above.

Figure 21:
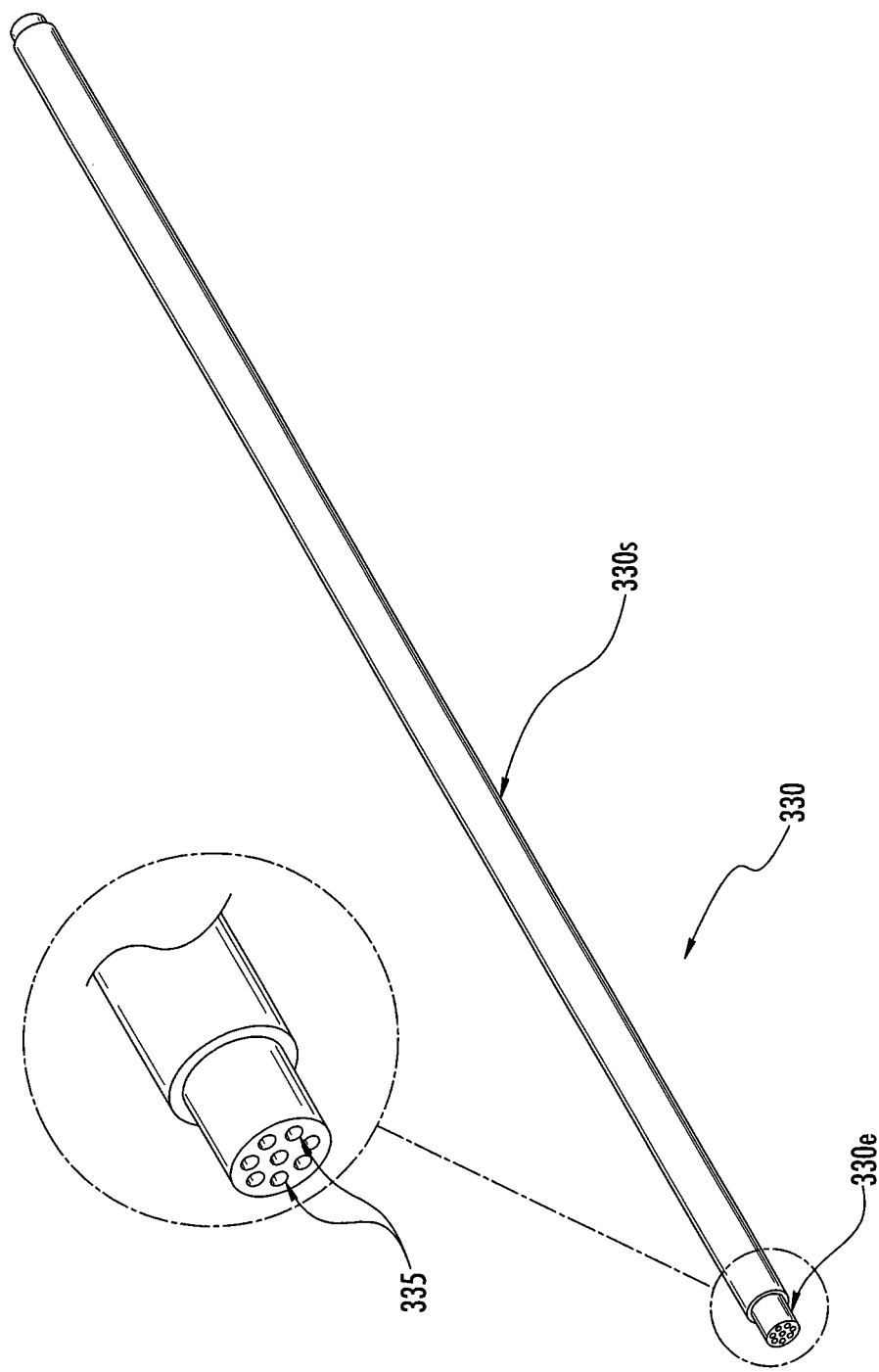
FIG. 21 illustrates a portion of an umbilical assembly according to some embodiments of the present invention.

An exemplary solid extrusion assembly 330 is illustrated in FIG. 21. The solid extrusion assembly 330 may form part of the umbilical assembly 120 described herein. More specifically, the solid extrusion assembly 330 may take the place of the conduit 130 and the tubes 135 (as well as the potting material 145 and/or the flexible member 140 where these components are used) in all embodiments described above and below. Thus, it will be understood that the solid extrusion assembly 330 may fit within the guide tube 125 and define the conduit with spaced-apart elongate passageways therein.

Still referring to FIG. 21, the solid extrusion assembly 330 includes a solid extrusion 330e. The solid extrusion is flexible with an outer wall and internal elongate channels or passageways 335 that define the spaced-apart passageways. Similar to the tubes 135 described in detail herein, the passageways 335 are in fluid communication with the chamber(s) 50. In particular, one passageway 335 is in fluid communication with the inlet 55 of a respective chamber 50 and another, different passageway 335 is in fluid communication with the outlet 60 of the respective chamber 50. In the illustrated embodiment, the solid extrusion 330e includes eight passageways 335, and is therefore configured for use with four chambers 50. The extrusion 330e may include greater or fewer than eight passageways 335 as needed.

As explained above, the extrusion assembly 330 may take the place of at least the conduit 130 in the umbilical assembly 120. Any differences between the extrusion assembly 330 and the conduit 130 will now be described.

As described above, the passageways 335 generally take the place of the flexible tubes 135. However, unlike the tubes 135, the passageways 335 may not extend all the way to the chamber(s) 50 and/or all the way to connection points outside the enclosure 15 (see FIGS. 15 and 16). Thus, in some embodiments, connectors (such as barbed connectors) may be included or used at one or both ends of each passageway 335. Connectors at a distal end of the passageways 335 may allow for tubing (which may be similar to the flexible tubing 135 described herein) to connect the passageways 335 with the inlet 55 and outlet 60 of the chamber(s) 50 (or the flange inlet and outlet paths 65, 70, where used). Similarly, connectors at a proximal end of the passageways 335 may allow for tubing (which may be similar to the flexible tubing 135 described herein) to connect the passageways 335 with components outside the enclosure 15, such as pumps or other tubing, which are described in more detail below.

In some embodiments, and as illustrated, the solid extrusion assembly 330 includes a sheath 330s. The sheath 330s material and configuration may have similar properties and provide similar advantages to the conduit 130 material and configuration described above. In particular, the sheath 330s may help withstand friction with the guide tube 125 and/or may help transfer torque during operation. In some embodiments, the sheath 330s may include ridges to minimize contact area with the guide tube 125 and/or to minimize friction during operation. The sheath 330s may be adhered to or may snugly fit around an outer wall of the solid extrusion 330e. In some embodiments, the sheath 330s and the solid extrusion 330e are sized and configured such that there is an interference fit (perhaps a substantial interference fit) between the two components. In this regard, the sheath 330s and the solid extrusion 330e may act as a single unit during operation (i.e., as the extrusion assembly 330). In some embodiments, the sheath 330s and the solid extrusion 330e may be integrated, and in some embodiments the sheath 330s may be omitted.

The solid extrusion assembly 330 may provide the same or substantially the same advantages as the conduit 130, tubes 135, and potting material 145 as described in detail above. Briefly, the passageways 335 may be positioned in the solid extrusion 330e such that they are spaced-apart from one another and/or from an outer wall of the extrusion 330e and/or from the sheath 330s, where used. The spaced-apart relationship may be maintained during operation, and therefore may help minimize movement/twisting of the passageways 335 relative to one another and/or may help minimize movement/twisting of the passageways 335 relative to the sheath 330s, where used. The result is a more robust umbilical assembly that can be used in "scaled-up" operations, as described in more detail above.

The solid extrusion 330e may comprise polymeric material, such as PVC, platinum-cured silicon, C-Flex, and other similar materials. The sheath 330s, where used, may comprise materials similar to those described above with regard to the conduit 130.

Again, to avoid repetition, the embodiments described above and below will only be described with the umbilical assembly 120 including the conduit 130 and the tubes 135 (and optionally the potting material 145 and/or the flexible member 140). However, it will be understood that the umbilical assembly 120 may include the extrusion assembly 330 or simply the extrusion 330e in place of the conduit 130, the tubes 135, and/or the potting material 145.

In some embodiments, and as illustrated in FIGS. 14A-D, a funnel 180 is provided on the rear side of the flange 35 and/or the door 20. The funnel 180 includes an opening 185 opposite the aperture 40. The funnel 180 is configured to accept at least part of the umbilical assembly 120. In the illustrated embodiments, the funnel 180 accepts the conduit 130, with the tubes 135 contained therein. The conduit 130 passes through the opening 185 and the aperture 40 such that at least the tubes 135 extend through the aperture 30. The tubes 135 can then be connected to additional components, as described in more detail below.

The funnel 180 can provide for reduced strain/stress on the conduit 130 and the tubes 135 where the conduit makes a final bend before extending through the aperture 30. In this regard, the funnel 180 provides a controlled bend of the conduit 130 and tubes 135 contained therein. This can reduce the chance of failure of the conduit 130 and/or the tubes 135 at what otherwise would be a high stress concentration point. The centerline of the opening 185 is preferably aligned or substantially aligned with the axis of rotation of the umbilical assembly 120; otherwise, additional, unnecessary loads could be applied to the conduit 130 and/or the tubes 135. Also, the funnel 180 preferably has a bend radius that is greater than the minimum dynamic bend radius of the conduit 130.

Moreover, the shape of the funnel 180 provides for a consistent bend of the conduit 130 and the tubes 135 contained therein while the umbilical assembly 120 is rotating during operation. The funnel 180 may be machined and/or polished to reduce friction or rubbing while the conduit 130 is rotating within the funnel 180. In addition, grease or other lubricous material may be applied to the funnel 180 to further reduce friction or rubbing. Additionally or alternatively, the funnel and/or the outer surface of the conduit 130 may be coated with a lubricous material such as Teflon® to reduce friction or rubbing.

Figure 15:
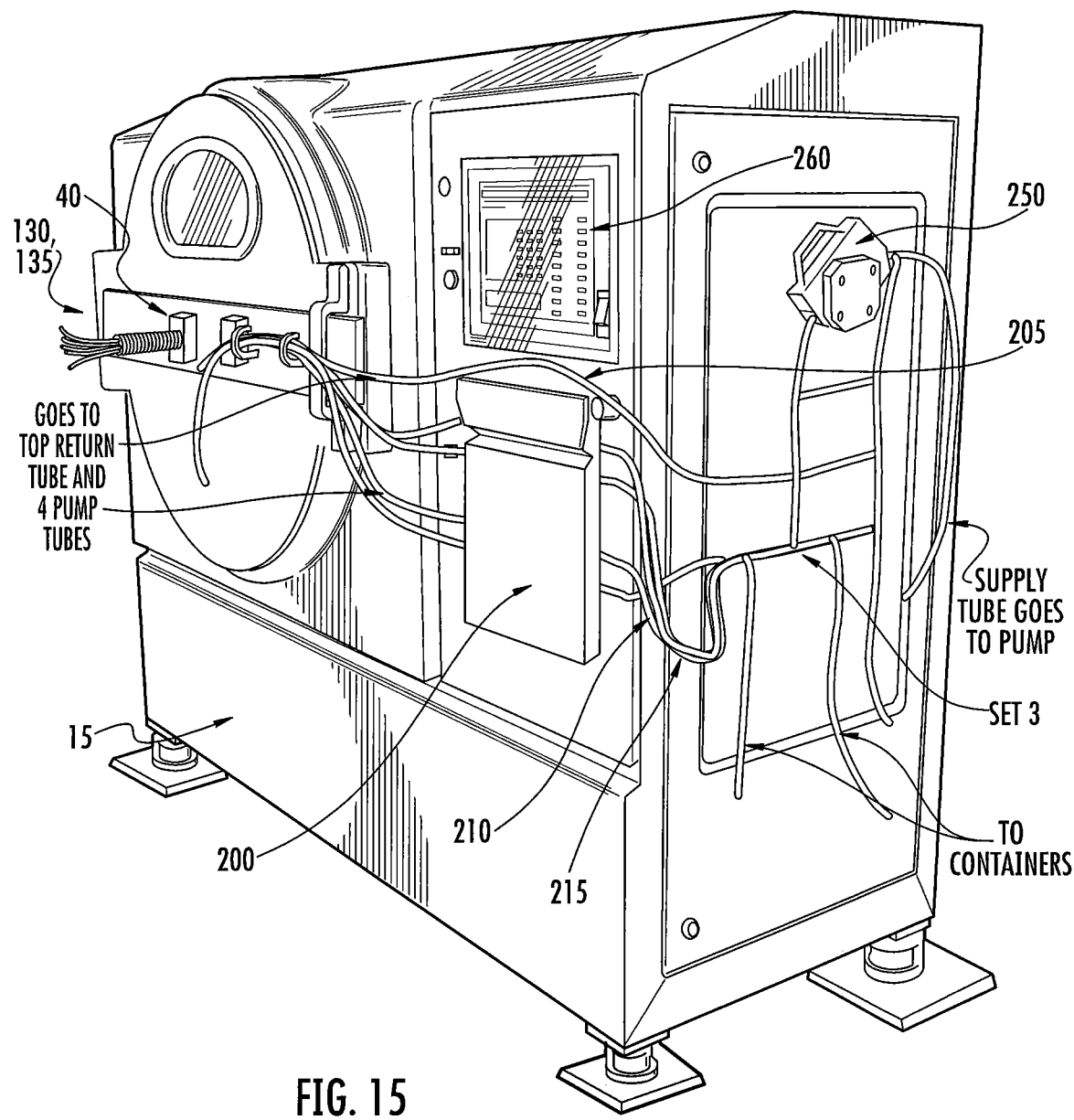
FIG. 15 is a perspective view of a system including disposable flow paths according to some embodiments of the present invention.
Figure 16:
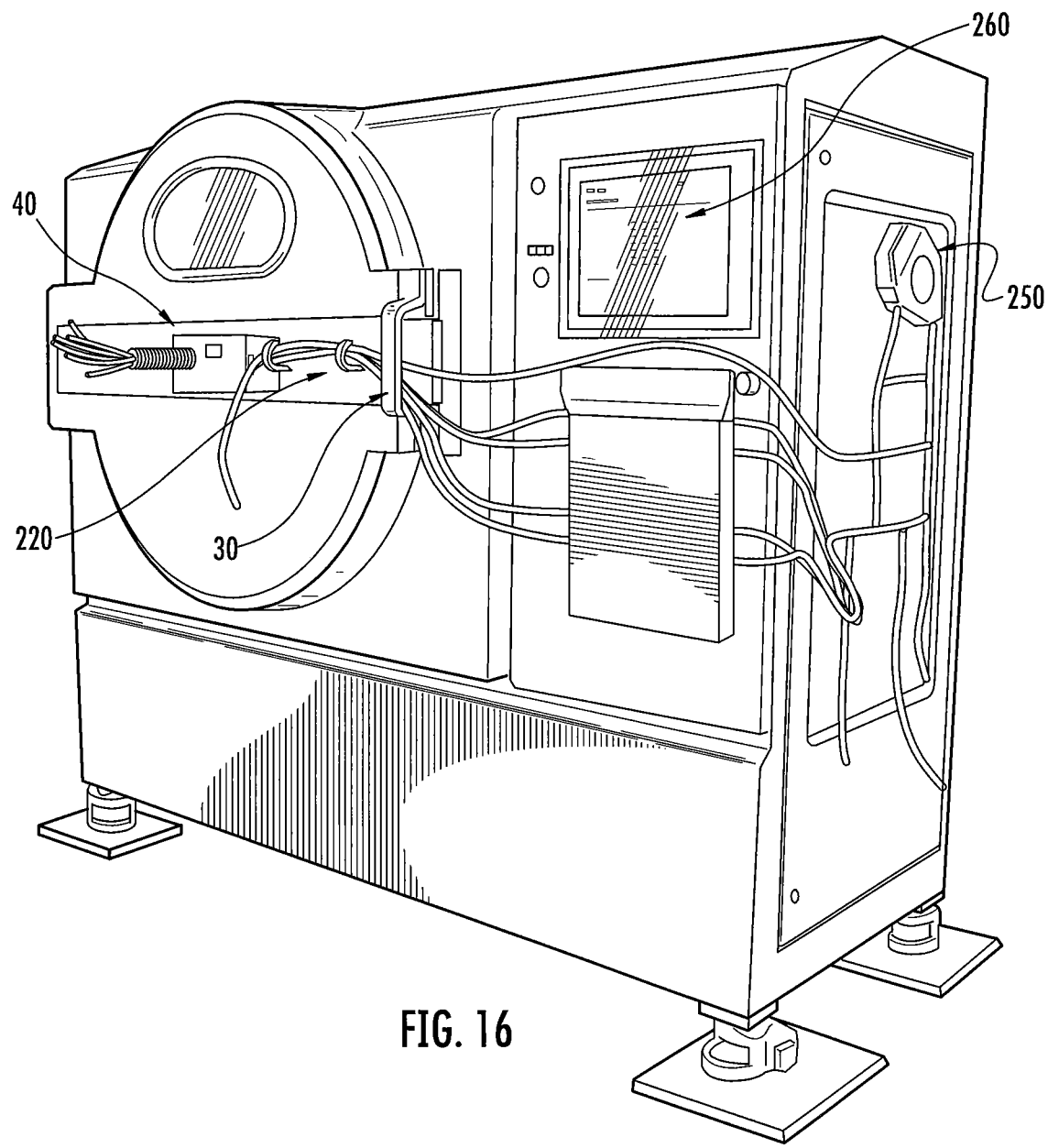
FIG. 16 is another perspective view of the system of FIG. 15.

Turning now to FIGS. 15 and 16, the conduit 130 and the tubes 135 are seen protruding from the aperture 40. At least one pump 200 may be provided on the enclosure 15 or on a panel thereon, or may be provided away from the enclosure 15. At least one valve may be provided on the enclosure 15 or on a panel thereon, or may be integrated with the tubing shown on the right side of the enclosure 15, or may be provided away from the enclosure 15. For example, one or more pinch valves may be provided on the enclosure 15, with the pinch valves configured to allow tubing to be inserted therethrough such that the tubing can be squeezed (or pinched) closed or partially closed.

Figure 17:
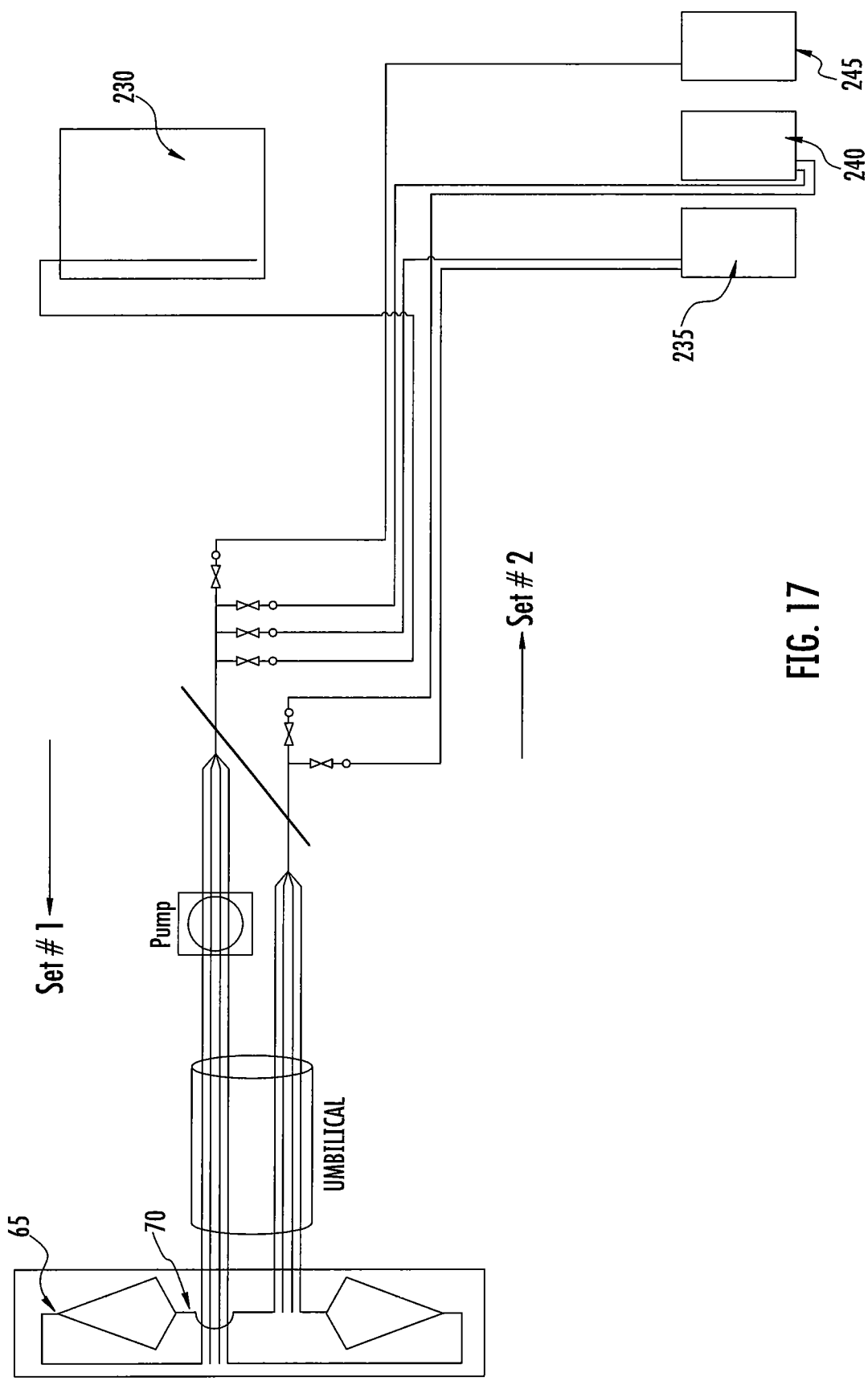
FIG. 17 is flow diagram illustrating operations according to some embodiments of the present invention.

FIG. 17 illustrates an exemplary flow diagram of the system. The system may include two sets: the chambers/umbilical set and the valve/fluid path set. The chambers/umbilical set may include at least the chamber(s) 50, the conduit 130, and the tubes 135 within the conduit 130. In the illustrated embodiment, the tubes 135 in fluid communication with the inlet paths 65 of the chambers 50 may connect with the pump 200 (see also FIGS. 15 and 16). Also in the illustrated embodiment, the tubes 135 in fluid communication with the outlet paths 70 of the chambers 50 may connect with at least one return tube 205 (see FIGS. 15 and 16). On the opposite side of the pump 200, tubes 210 may connect with a harness or manifold 215, which connects the chambers/umbilical set with the valve/fluid path set. In some embodiments, the two disposable sets can be connected by a sterile tube welding process. The disposable sets can be supplied sealed and/or sterilized. By employing a sterile tube welding process, the disposable sets can be connected without using any sort of connector (e.g., harness, manifold, etc.), and the disposable sets do not need to be "opened," which could result in a loss of sterility.

The valve/fluid path set typically comprises tubing and/or valves, which may be integrated with the tubing. In some embodiments, the valve/fluid path set is configured to be routed through one or more valves, such as pinch valves included on the enclosure, for example. In the embodiment illustrated in FIGS. 15 and 16, the valve/fluid path set includes the tubing seen on the right side of the enclosure 15. In some embodiments, the valve/fluid path set includes the return tube(s) 205. It is noted that, although the tubes are shown as "broken" in FIGS. 15 and 16, the tubes 135 protruding from the aperture 40 of the flange 35 will typically connect with the pump 200 and/or the return tube(s) 205. The return tube(s) 205 and/or the tubes 135 running to the pump 200 may be routed through the handle 30 of the door 20 and/or kept in place by one or more holders 220, such as hooks.

As seen in the flow diagram of FIG. 17, the valve/fluid path set can connect to various containers, such as a bioreactor 230, a waste media container 235, a clean media container 240, and/or a cell harvest container 245. The various containers will typically be located away from the enclosure 15, although at least some of the containers may be contained within the enclosure 15 in some embodiments. In the embodiment illustrated in FIGS. 15 and 16, the lower (open) portions of the tubes on the right side of the enclosure 15 may connect with various containers, such as the containers described above. The valve/fluid path set may be configurable to perform various operations, as will be summarized in more detail below. At least one secondary pump 250 may be included on the enclosure 15 or away from the enclosure 15; the secondary pump 250 may be useful in at least some of these various operations.

At least some of the components described herein may be disposable. For example, the chambers 50, the conduit 130, and/or the tubes 135 contained therein may be disposable. As described above, the disposable chambers 50 may be constructed of a flexible or resilient polymer, such as a transparent or translucent polymer, thereby forming a "bag chamber." In some embodiments, the disposable chambers 50 may be thermoformed. In some embodiments, the material of the disposable chambers 50 may be relatively thin (e.g., less than 1 mm thick medical grade PVC). In other embodiments, the material of the disposable chambers 50 may be another material (e.g., FEP, C-Flex, blow molded EVA, low-density polyethylene, etc.), to permit compliance with good manufacturing practice (cGMP). The disposable chambers 50 may include inlet and outlet fluid paths 65, 70 (which may be integrated), as illustrated in FIG. 5A, and as described in more detail above. The chamber holders 75 (see FIG. 5B) can inhibit failure of the disposable chambers 50 by accommodating the majority of or all of the loads experienced due to rotation of the rotor 45 and the chambers 50.

A system comprising two separate disposable fluid paths is also contemplated. In this system, the two sets described above (i.e., the chambers/umbilical set and the valve/fluid path set) may be separately disposable. For example, referring to FIGS. 15-17, the chambers 50, the conduit 130, and the tubes 135 contained therein (leading up to or extending just past the pump 200) may comprise a first disposable flow path (Set #1). The tubing and/or valves to the right of the harness or manifold 215 may comprise a second disposable flow path (Set #2). The return tube(s) 205 will typically be included in disposable Set #2, but may be included in either disposable flow path.

The disposable fluid path(s) can provide advantages over conventional continuous flow centrifuges and like apparatus. Systems that do not employ disposable flow paths generally have to adhere to Cleaning-in-Place (CIP) and Sterilization-in-Place (SIP) procedures and standards. This is especially the case for those systems that perform operations that are sensitive to contamination, such as cell culturing/harvesting and blood processing, for example. The disposable flow paths described herein can eliminate the need to perform CIP and SIP procedures. Furthermore, the use of completely disposable fluid paths permits compliance with good manufacturing practice (cGMP). The paths can be provided as sterile components ready for insertion and use.

As discussed above, the systems disclosed herein can be used to perform a number of processing, harvesting, etc. methods and operations. Exemplary methods and operations are disclosed in detail in co-pending and commonly owned International Application Nos. PCT/US2009/004113 (International Publication No. WO 2010/008563) and PCT/US2009/004137 (International Publication No. WO 2010/008579), both filed Jul. 16, 2009, the disclosures of each of which are hereby incorporated by reference herein in their entirety. A brief overview of some of the methods and operations follow, with reference to FIG. 17.

In continuous flow centrifugation operations, media containing particles such as cells will be fed in the rotating chambers 50 to form a fluidized bed of cells. After the chambers 50 are filled with cells, the flow will be reversed to empty out the chambers 50. The system (i.e., the rotors and the chambers) does not need to stop rotating throughout this application. The cycle can be repeated to concentrate cells from large volumes.

Similarly, in perfusion operations, particles such as cells are immobilized in the rotating chambers 50 in fluidized beds for culturing and/or harvesting. For example, cells and media may be removed from the bioreactor 230 and transported to the chambers 50. A continuous flow of media and cells substantially opposes the centrifugal force created by the rotating chambers 50, thereby immobilizing the cells in a fluidized bed. Using a perfusion cycle, the cells are provided with fresh media continuously and spent media is removed, such as to the waste container 235. The cells can then be removed from the chambers 50, perhaps by reversing the fluid flow and returning the cells to the bioreactor 230 or the cell harvest container 245.

The systems disclosed herein can also perform media exchanges during cell culture or harvest. In this application, cell culture is first fed to the rotating chambers 50 to form a bed of fluidized cells, and then a new media or buffer is fed through the inlet paths 65 of the chambers 50 to be perfused through the bed. For example, the new media or buffer may be introduced from the clean media container 240. After the cells are washed with the media or buffer, the chambers 50 are emptied out by reversing the flow (i.e., introducing media to the outlet paths 70 of the chambers 50). It is noted that the media/buffer exchange application could be used prior to additional processes such as transfection, cell dispensing, seeding a bioreactor, etc.

The systems are also capable of separating population of cells based on density and/or size. In this application, fluid containing different populations of cells will be fed into the rotating chambers 50. Cells will be separated by modulating the fluid feed rate and/or the centrifugal force (i.e., the rotational speed of the rotor). Once the fluid feed rate and centrifugal forces are adjusted appropriately, lighter/smaller cells will exit out of the chambers 50 with media. After a cell bed is formed, fresh media or buffer could be used to separate another population by once again adjusting the feed rate and/or centrifugal force. This process can be repeated several times to separate multiple populations of cells that differ by density and/or size. Finally heavier/larger cells are harvested by reversing the flow of fresh media.

These are just a sampling of the processes that can be performed by the disclosed systems. Other processes include cell dispensing, transfection, eletroporation, selection/purification/enrichment (such as by using affinity matrices), fractionation of proteins/biomaterials, associating particles with and/or removing particles from scaffolding material, and coating particles. These processes are described in detail in the aforementioned applications.

Referring again to FIGS. 15 and 16, a display 260 may be provided on the enclosure 15, or may be provided on a panel attached or adjacent to the enclosure 15, or may be provided away from the enclosure 15. The display 260 is connected (e.g., directly or wirelessly) to at least one controller (not shown). There may be controllers associated with the various components of the system, including the motor, the pump(s), the valves, etc. There may be one controller associated with all components or certain components may have dedicated controllers.

Figure 20:
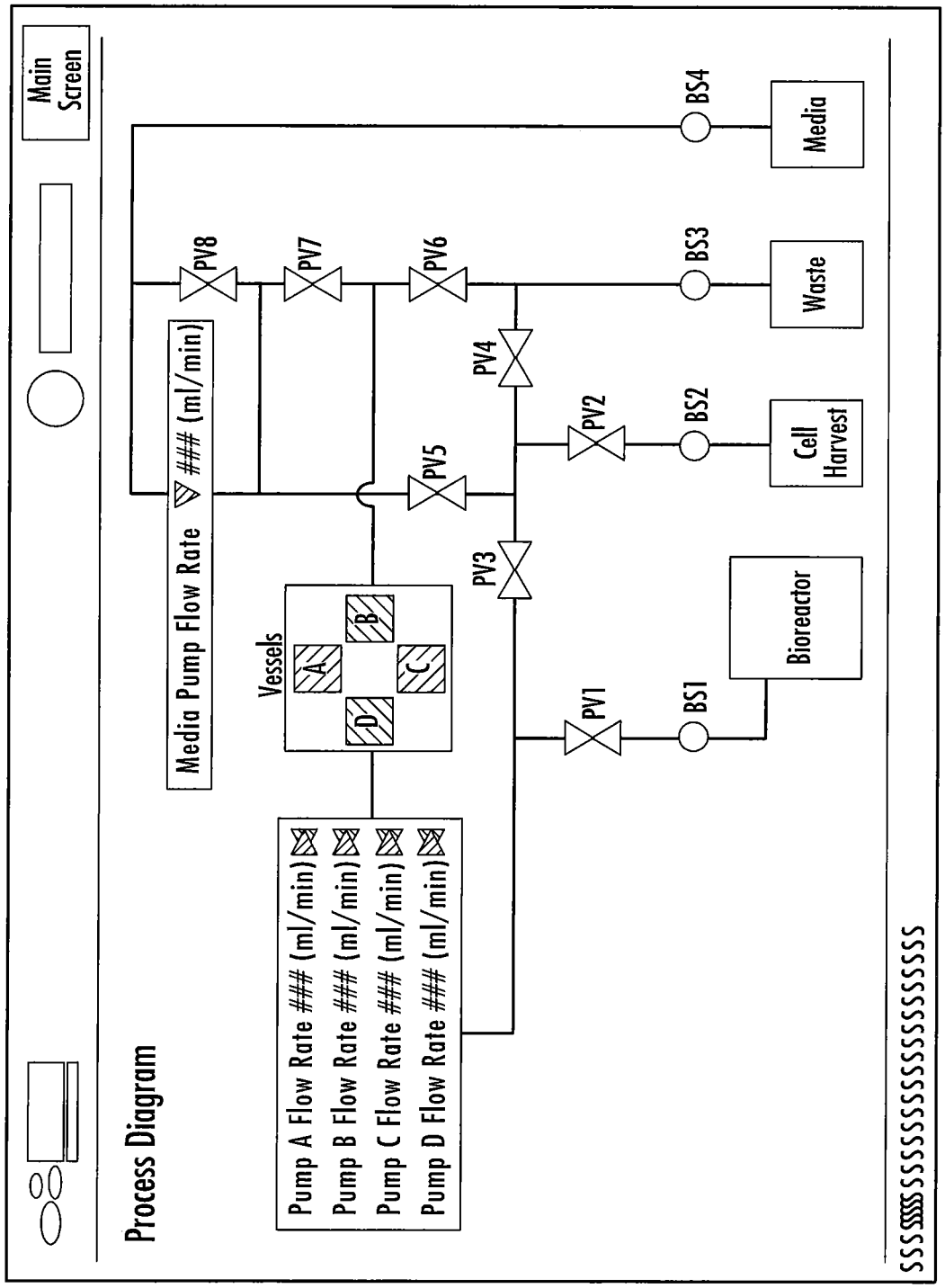

Simulated screenshots of the display 260 are illustrated in FIGS. 18-20. The display 260 may allow parameters to be entered and data or progress to be read by an operator. The display may include touch screen buttons that dictate the operation of various components, as seen in FIG. 18. In some embodiments, there is a separate user input device such as a keyboard; in other words, the display may not employ a touch screen.

In some embodiments, a light source and/or a camera may be included on the enclosure or in the interior cavity of the enclosure. The light source and/or the camera may be useful to illuminate the chamber(s) and/or capture images of the chamber(s) (e.g., the interior of the chamber(s) during operation). The captured images may be useful to provide feedback to the operator and/or the system as to the progress of the particular process taking place within the chamber(s). The camera may be in communication with the display (either directly or via a controller), such that the images may be transmitted to the display, for example. The controller(s) and/or software associated with the controller(s) may automatically correlate captured images with a particular chamber.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. An apparatus for manipulating particles, the apparatus comprising:
   a rotor rotatable at a speed about an axis, the rotor having an outer periphery and front and rear opposite sides;
   at least one chamber mounted on the rotor, each chamber having an inlet and an opposed outlet;
   an umbilical assembly rotatable about the axis, the umbilical assembly comprising:
      a curvilinear guide connecting to the rear side of the rotor;
      a flexible conduit residing in the guide; and
      first and second elongate passageways for each chamber extending through the conduit, wherein the first passageway is in fluid communication with the inlet of a respective chamber and the second passageway is in fluid communication with the outlet of the respective chamber; and
   a drive mechanism configured to rotate the umbilical assembly at about one-half the speed of the rotor;
   wherein each chamber comprises a substantially conical body portion and a flange extending about at least a portion of a perimeter of the conical body portion, the flange defining a plane and the conical body portion extending outwardly from the plane, the flange including an inlet fluid path that is external to the conical body portion and extends around at least a portion of the perimeter of the conical body portion to the chamber inlet and an outlet fluid path that extends from the chamber outlet, and wherein the first elongate passageway is in fluid communication with the flange inlet fluid path and the second elongate passageway is in fluid communication with the flange outlet fluid path,
   wherein each chamber is configured to allow fluid flow therethrough while the rotor and the chamber rotate about the axis such that a force of fluid flowing from the inlet to the outlet opposes a centrifugal force created by the rotation of the rotor and the chamber,
   wherein a fluid flow path from the inlet to the outlet is perpendicular to the axis.

2. The apparatus of claim 1, wherein the first and second passageways for each chamber comprise corresponding first and second flexible tubes.

3. The apparatus of claim 2, wherein the first tube connects with the flange inlet fluid path of a respective chamber and the second tube connects with the flange outlet fluid path of the respective chamber.

4. The apparatus of claim 1, wherein each chamber is a translucent or transparent fluid chamber.

5. The apparatus of claim 1, wherein each chamber is disposable.

6. The apparatus of claim 1, wherein the drive mechanism comprises gears.

7. The apparatus of claim 1, wherein the curvilinear guide is configured to extend about the outer periphery of the rotor.

8. The apparatus of claim 1, wherein the inlet of each chamber is at an apex of the conical body portion.

9. The apparatus of claim 8, wherein the outlet of each chamber is proximate a base of the conical body portion.

10. A method of manipulating particles, the method comprising:
    providing the apparatus of claim 1;
    rotating the rotor and the at least one chamber at a first speed, thereby creating a centrifugal force field;
    rotating the umbilical assembly at a second speed, wherein the second speed is about one-half the first speed, thereby inhibiting the first and second passageways for each chamber from fully twisting;
    flowing media and particles into a respective chamber using the first passageway, wherein a continuous flow of media and particles creates a fluid force that substantially opposes the centrifugal force field, thereby immobilizing at least some of the particles in a fluidized bed in the respective chamber; and
    flowing media out of the respective chamber and through the second passageway.

11. A centrifugal fluid processing system, the system comprising:
    a housing having an interior cavity with an access aperture extending from an external surface of the housing to the interior cavity;
    at least one chamber having an inlet and an opposed outlet held on a rotor in the interior cavity;
    a substantially rigid curvilinear guide extending around an outer periphery of the rotor in the interior cavity;
    a plurality of elongate passageways in the guide, the plurality of passageways extending from a location that is external to the housing through the access aperture and into the interior cavity, wherein the plurality of passageways includes first and second passageways for each chamber, and wherein the first passageway is in fluid communication with the inlet of a respective chamber and the second passageway is in fluid communication with the outlet of the respective chamber; and a drive mechanism configured to rotate the guide at a first speed and the rotor and the at least one fluid chamber about an axis at a second speed, wherein the second speed is about twice the first speed, wherein each chamber comprises a substantially conical body portion and a flange extending about at least a portion of a perimeter of the conical body portion, the flange defining a plane and the conical body portion extending outwardly from the plane, the flange including an inlet fluid path that is external to the conical body portion and extends around at least a portion of the perimeter of the conical body portion to the chamber inlet and an outlet fluid path that extends from the chamber outlet, wherein each chamber is configured to allow fluid flow therethrough while the rotor and the chamber rotate about the axis such that a force of fluid flowing from the inlet to the outlet opposes a centrifugal force created by the rotation of the rotor and the chamber, wherein a fluid flow path from the inlet to the outlet is perpendicular to the axis.

12. The system of claim 11, wherein the first and second passageways for each chamber comprise corresponding first and second flexible tubes.

13. The system of claim 12, wherein the first tube connects with the flange inlet fluid path of a respective chamber and the second tube connects with the flange outlet fluid path of the respective chamber.

14. The system of claim 11, wherein the inlet of each chamber is at an apex of the conical body portion.

15. The system of claim 14, wherein the outlet of each chamber is proximate a base of the conical body portion.

16. The system of claim 11, wherein:
the at least one chamber comprises first and second chambers;
the first and second passageways for each chamber comprise first through fourth flexible tubes;
the first tube is in fluid communication with the inlet of the first chamber and the second tube is in fluid communication with the outlet of the first chamber;
the third tube is in fluid communication with the inlet of the second chamber and the fourth tube is in fluid communication with the outlet of the second chamber.

17. The system of claim 11, wherein each chamber is disposable.

18. The system of claim 11, wherein the drive mechanism comprises gears.

19. The system of claim 11, further comprising an enclosure comprising the housing and a door coupled to the housing, wherein the door is configured to be moved between a closed position and an open position.

20. The system of claim 19, wherein, in the open position, the door provides access to the interior cavity of the housing.

21. The system of claim 20, further comprising a window on the door, wherein, in the closed position, the window is configured to provide visual access to the at least one chamber.

22. The system of claim 19, further comprising a display on the enclosure, the display configured to display operational data and/or parameters of the system.

23. The system of claim 11, wherein each chamber is a translucent or transparent fluid chamber.

* * * * *